(12) United States Patent
Lee et al.

(10) Patent No.: US 11,883,319 B2
(45) Date of Patent: Jan. 30, 2024

(54) MANDIBULAR ADVANCEMENT APPARATUS

(71) Applicant: OUaR Lab, Inc., Seoul (KR)

(72) Inventors: Jae Gun Lee, Bucheon-si (KR); Won Hyuck Yoon, Seoul (KR)

(73) Assignee: OUaR Lab, Inc., Seoul (KR)

( * ) Notice: Subject to any disclaimer, the term of this patent is extended or adjusted under 35 U.S.C. 154(b) by 263 days.

(21) Appl. No.: 17/511,071

(22) Filed: Oct. 26, 2021

(65) Prior Publication Data

US 2023/0125589 A1    Apr. 27, 2023

(51) Int. Cl.
*A61F 5/56*     (2006.01)
*A61B 5/08*     (2006.01)

(52) U.S. Cl.
CPC .............. *A61F 5/566* (2013.01); *A61B 5/08* (2013.01); *A61B 2562/0247* (2013.01); *A61B 2562/0271* (2013.01)

(58) Field of Classification Search
CPC ............ A63B 71/085; A63B 2071/086; A63B 2071/088; A61F 2005/563; A61F 5/56; A61F 5/566; A61C 7/08; A61C 7/36
See application file for complete search history.

(56) References Cited

FOREIGN PATENT DOCUMENTS

JP    2012-528698 A    11/2012
KR    101784416 B1     11/2017

*Primary Examiner* — Camtu T Nguyen
(74) *Attorney, Agent, or Firm* — NKL Law; Jae Youn Kim

(57) ABSTRACT

Provided is a mandibular advancement device including: a driving unit including an intraoral device; a main body configured to generate a driving force for driving the driving unit; and a connection unit configured to connect the driving unit and the main body to transmit the driving force generated by the main body to the driving unit, wherein the driving unit includes a driving case having an empty space therein, a coupling unit having fixed thereto the intraoral device and coupled to a front of the driving case, and a rear cover coupled to a rear of the driving case and accommodating a piston therein, the intraoral device includes a first frame and a second frame located to overlap each other, a first seating portion covering a portion of the first frame located in an oral cavity of a user, a second seating portion covering a portion of the second frame located in the oral cavity of the user, and a fixing unit coupled to the first frame and the second frame, the first frame is coupled to the fixing unit to be relative movable with respect to the second frame, the second frame is fixed to the fixing unit, and the fixing unit is fixed to the coupling unit.

4 Claims, 18 Drawing Sheets

MANDIBULAR ADVANCEMENT APPARATUS

STATEMENT REGARDING PRIOR DISCLOSURES BY THE INVENTOR(S)

The following disclosures are submitted under 3 U.S.C. 102(b)(1)(A) as prior disclosures by, or on behalf of, the inventor(s) of the present application: Korean patent application publications KR 10-2021-0046440A published on Apr. 28, 2021, KR 10-2021-0046441A published on Apr. 28, 2021, and KR 10-2021-0046442A published on Apr. 28, 2021.

TECHNICAL FIELD

Embodiments of the present disclosure relate to a mandibular advancement device.

BACKGROUND ART

Obstructive sleep apnea (OSA) is a disorder characterized by repeated episodes of upper airway closure during sleep. The patients with OSA show loud snoring accompanied with gasping, followed by periods of silence when breathing stops or nearly stop. Apnea can cause awakenings during sleep and sleep fragmentations, which may lead to various psychoneurological complications. Apnea frequently lead to daytime sleepiness, cognitive impairment, decreased job performance, and reduced quality of life, hypertension, cardiovascular diseases, and abnormal glucose metabolism.

OSA can be treated or symptoms thereof can be alleviated, through surgical or non-surgical treatments. One of the non-surgical treatments is an instrumental therapy. The instrumental therapy may include: a continuous positive airway pressure (CPAP) therapy, in which air is applied into the airway from the outside; and a therapy using oral appliances worn in the oral cavity to pull the lower jaw forward. However, in the case of the CPAP therapy, the patients may be uncomfortable due to abdominal distension or nasal obstruction, caused by the air injected from the outside, and it is difficult to carry the CPAP device while traveling. Since the lower jaw is kept advanced forward during sleep, the oral appliances can cause the altered bite, excessive saliva or pain in the teeth and temporomandibular joint.

DESCRIPTION OF EMBODIMENTS

Technical Problem

To solve the above-stated problems, embodiments of the present disclosure provide a mandibular advancement device that automatically operates only when obstructive sleep apnea is sensed or when sleep apnea is highly likely to occur.

Solution to Problem

According to an embodiment of the present disclosure, a mandibular advancement device includes a driving unit including an intraoral device; a main body configured to generate a driving force for driving the driving unit; and a connection unit configured to connect the driving unit and the main body to transmit the driving force generated by the main body to the driving unit, wherein the driving unit includes a driving case having an empty space therein, a coupling unit having fixed thereto the intraoral device and coupled to a front of the driving case, and a rear cover coupled to a rear of the driving case and accommodating a piston therein, the intraoral device includes a first frame and a second frame located to overlap each other, a first seating portion covering a portion of the first frame located in an oral cavity of a user, a second seating portion covering a portion of the second frame located in the oral cavity of the user, and a fixing unit coupled to the first frame and the second frame, the first frame is coupled to the fixing unit to be relative movable with respect to the second frame, and the second frame is fixed to the fixing unit, and the fixing unit is fixed to the coupling unit.

In the present embodiment, the piston may include a piston head disposed in the rear cover and a push arm protruding from the center of the piston head toward the fixing unit, and, when the piston is moved by the driving force, the push arm may push the first frame.

In the present embodiment, upper teeth of the user may be seated on the first seating portion, lower teeth of the user may be seated on the second seating portion, and the second frame and the driving case may be moved backward by a force pushing the first frame.

In the present embodiment, the piston may further include a fitting protrusion protruding in a direction perpendicular to a direction in which the push arm extends, the driving unit may further include a lower cover coupled to the bottom surface of the driving case, a rod and a guide covering the rod may be arranged on the lower cover, the guide may include a hole extending in one direction, and the rod may protrude to the outside of the guide through the hole and be coupled with the fitting protrusion.

In the present embodiment, the driving unit may further include a sensing unit configured to sense user information, and the main body may include a control unit configured to control an operation of the driving unit according to a sensing result sensed by the sensing unit.

In the present embodiment, the driving force may be compressed air, the main body may further include a pump configured to generate the compressed air, a first pipe and a second pipe configured to transmit the compressed air from the pump to the connection unit, and a valve configured to block a flow of the compressed air between the first pipe and the second pipe, and the control unit may control the operation of the driving unit by controlling operations of the pump and the valve.

According to another embodiment of the present disclosure, a mandibular advancement device includes a driving unit including an intraoral device; a main body configured to generate a driving force for driving the driving unit; and a connection unit configured to connect the driving unit and the main body to transmit the driving force generated by the main body to the driving unit, wherein the intraoral device includes a guide and a first frame and a second frame that are coupled to the guide, the first frame is inserted into the guide and is coupled to the guide to be movable in a first direction, the second frame has a shape bent along a front surface and a bottom surface of the guide facing the second frame, a supporting unit, which is an end portion of the guide, is disposed to face the bottom surface of the guide, and a spring is provided between the supporting unit and the guide, such that the second frame is movable in a vertical direction.

In the present embodiment, the second frame may further include a rail protruding toward the guide and extending in the vertical direction at a bent portion of the second frame facing the front surface of the guide, and a rail groove to which the rail is sliding-fastened in the vertical direction may be formed in the front surface of the guide.

In the present embodiment, the driving unit may further include a power transmission unit detachably coupled to the intraoral device, the power transmission unit may include a body having an empty space therein and a cylinder coupled to the rear of the body and accommodating a piston therein, the piston includes a piston head disposed inside the cylinder and a piston rod protruding from the center of the piston head toward the intraoral device, and, when the piston is moved by the driving force, the piston rod may penetrate through the front surface of the body and push the first frame in the first direction.

In the present embodiment, the body may include a plurality of grooves extending from an end of the body in the lengthwise direction of the body, the piston may include at least two support beams protruding in a direction perpendicular to a direction in which the piston rod extends and located in the plurality of grooves, and, when the piston moves, the at least two support beams may move along the plurality of grooves.

In the present embodiment, the power transmission unit may further include at least one dial provided to surround the outer surface of the body, the inner surface of the dial includes a first region and a second region having different heights, a boundary between the first region and the second region may be formed, such that a distance from any one edge thereof gradually decreases along the circumference of the dial, a thickness of the first region is smaller than a thickness of the second region, and the at least two support beams may contact the first region.

In the present embodiment, when the dial is rotated, the at least two support beams may be pushed by the second region at the boundary and be moved along the grooves.

In the present embodiment, a first seating portion on which upper teeth of a user are seated may be formed at the first frame, a second seating portion on which lower teeth of the user are seated may be formed at the second frame, and the second frame and the body may be moved in a direction opposite to the first direction by a force pushing the first frame.

In the present embodiment, the driving force may be compressed air, the main body may further include a pump configured to generate the compressed air, a first pipe and a second pipe configured to transmit the compressed air from the pump to the connection unit, and a valve configured to adjust a flow of the compressed air between the first pipe and the second pipe and a control unit that controls the operation of the driving unit by controlling operations of the pump and the valve.

According to another embodiment of the present disclosure, a mandibular advancement device includes a driving unit including an intraoral device and a power transmission unit coupled to the intraoral device; a main body configured to generate a driving force for driving the driving unit; and a connection unit configured to connect the driving unit and the main body to transmit the driving force generated by the main body to the driving unit, the intraoral device includes a first frame, a second frame, and a guide coupled to the first frame and the second frame, the first frame is inserted into the guide and is coupled to the guide to be movable in a first direction, the second frame is coupled to the guide to be movable together with the guide in the first direction, and the power transmission unit is detachably coupled to the guide.

In the present embodiment, the power transmission unit may include a body having an empty space therein and a fastening protrusion protruding from the front surface of the body toward the driving unit and including an end portion having a round shape when viewed from above, the guide may include a pair of latches surrounding the end portion of the fastening protrusion from both sides and a pair of latch springs that respectively apply forces to the pair of latches, and the pair of latches may be closed along side surfaces of the fastening protrusion and fastened to the fastening protrusion.

In the present embodiment, the pair of latches may each include a locking protrusion protruding outward, and, when the latch springs are compressed by at least one of the locking protrusions, the pair of latches may be opened from each other, and thus the fastening with the fastening protrusion may be released.

In the present embodiment, the power transmission unit may further include a cylinder coupled to the rear of the body and accommodating a piston therein, the body may include a plurality of grooves extending from an end of the body in the lengthwise direction of the body, the piston may include a piston head disposed inside the cylinder, a piston rod protruding from the center of the piston head toward the seating portions, and at least two support beams protruding in a direction perpendicular to a direction in which the piston rod extends and located in the plurality of grooves, and, when the piston is moved by the driving force, the at least two support beams may move along the plurality of grooves.

In the present embodiment, the power transmission unit may further include at least one dial provided to surround the outer surface of the body, the inner surface of the dial includes a first region and a second region having different heights, a boundary between the first region and the second region may be formed, such that a distance from any one edge thereof gradually decreases along the circumference of the dial, a thickness of the first region is smaller than a thickness of the second region, and the at least two support beams may contact the first region.

In the present embodiment, when the dial is rotated, the at least two support beams may be pushed by the second region at the boundary and be moved along the grooves.

In the present embodiment, a first seating portion on which upper teeth of a user are seated may be formed at the first frame, a second seating portion on which lower teeth of the user are seated may be formed at the second frame, and, when the piston is moved by the driving force, the second frame, the guide, and the body may be moved in a direction opposite to the first direction by a force of the piston rod pushing the first frame.

In the present embodiment, the driving force may be compressed air, the main body may further include a pump configured to generate the compressed air, a first pipe and a second pipe configured to transmit the compressed air from the pump to the connection unit, and a valve configured to adjust a flow of the compressed air between the first pipe and the second pipe and a control unit that controls the operation of the driving unit by controlling operations of the pump and the valve.

Advantageous Effects of Disclosure

According to embodiments of the present disclosure, a mandibular advancement device operates only when obstructive sleep apnea is sensed during sleep or sleep apnea is highly likely to occur, and thus user discomfort caused by wearing the mandibular advancement device, e.g., pain and salivation, may be reduced.

Also, since a driving unit including an intraoral device put in the oral cavity of a user and a main body providing a driving force for driving the driving unit are separated from each other, the weight of the driving unit is reduced, thereby minimizing discomfort caused by wearing the mandibular advancement device.

According to the embodiments of the present disclosure, even when the mouth is opened during sleep, a mandibular advancement device is prevented from being separated, thereby improving the effect of using the mandibular advancement device.

Also, since a driving unit including an intraoral device put in the oral cavity of a user and a main body providing a driving force for driving the driving unit are separated from each other, the weight of the driving unit is reduced, thereby minimizing discomfort caused by wearing the mandibular advancement device. Also, the intraoral device may be easily separated, thereby facilitating cleaning of seating portions.

MODE OF DISCLOSURE

Figure 1:
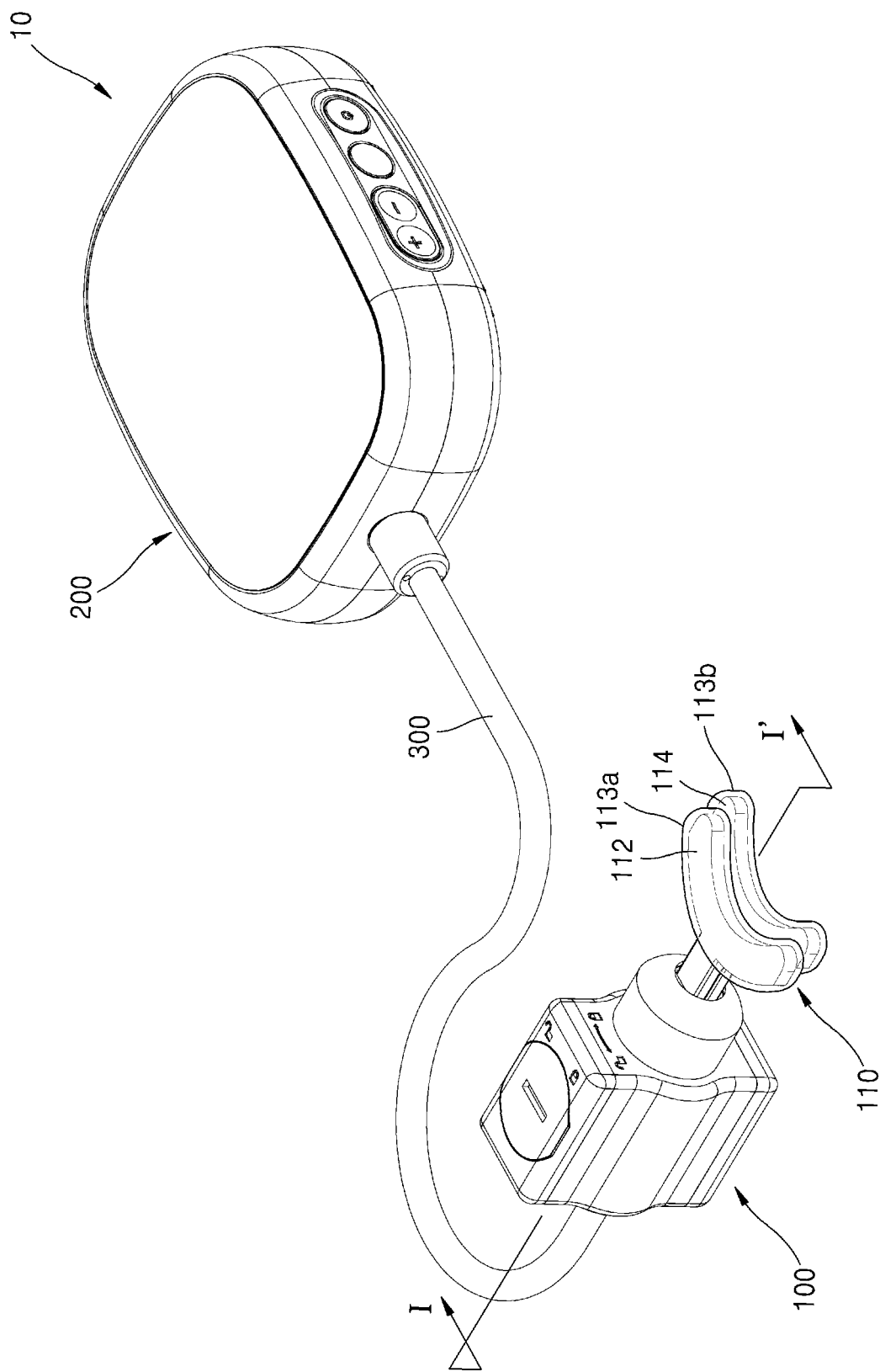
FIG. 1 is a schematic perspective view of a mandibular advancement device according to an embodiment of the present disclosure.

The present disclosure may include various embodiments and modifications, and embodiments thereof will be illustrated in the drawings and will be described herein in detail. The effects and features of the present disclosure and the accompanying methods thereof will become apparent from the following description of the embodiments, taken in conjunction with the accompanying drawings. However, the present disclosure is not limited to the embodiments described below, and may be embodied in various modes.

Reference will now be made in detail to embodiments, examples of which are illustrated in the accompanying drawings. In the drawings, the same elements are denoted by the same reference numerals, and a repeated explanation thereof will not be given.

It will be understood that although the terms "first", "second", etc. may be used herein to describe various elements, these elements should not be limited by these terms. These elements are only used to distinguish one element from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

Sizes of elements in the drawings may be exaggerated for convenience of explanation. In other words, since sizes and thicknesses of components in the drawings are arbitrarily illustrated for convenience of explanation, the following embodiments are not limited thereto.

Figure 2:
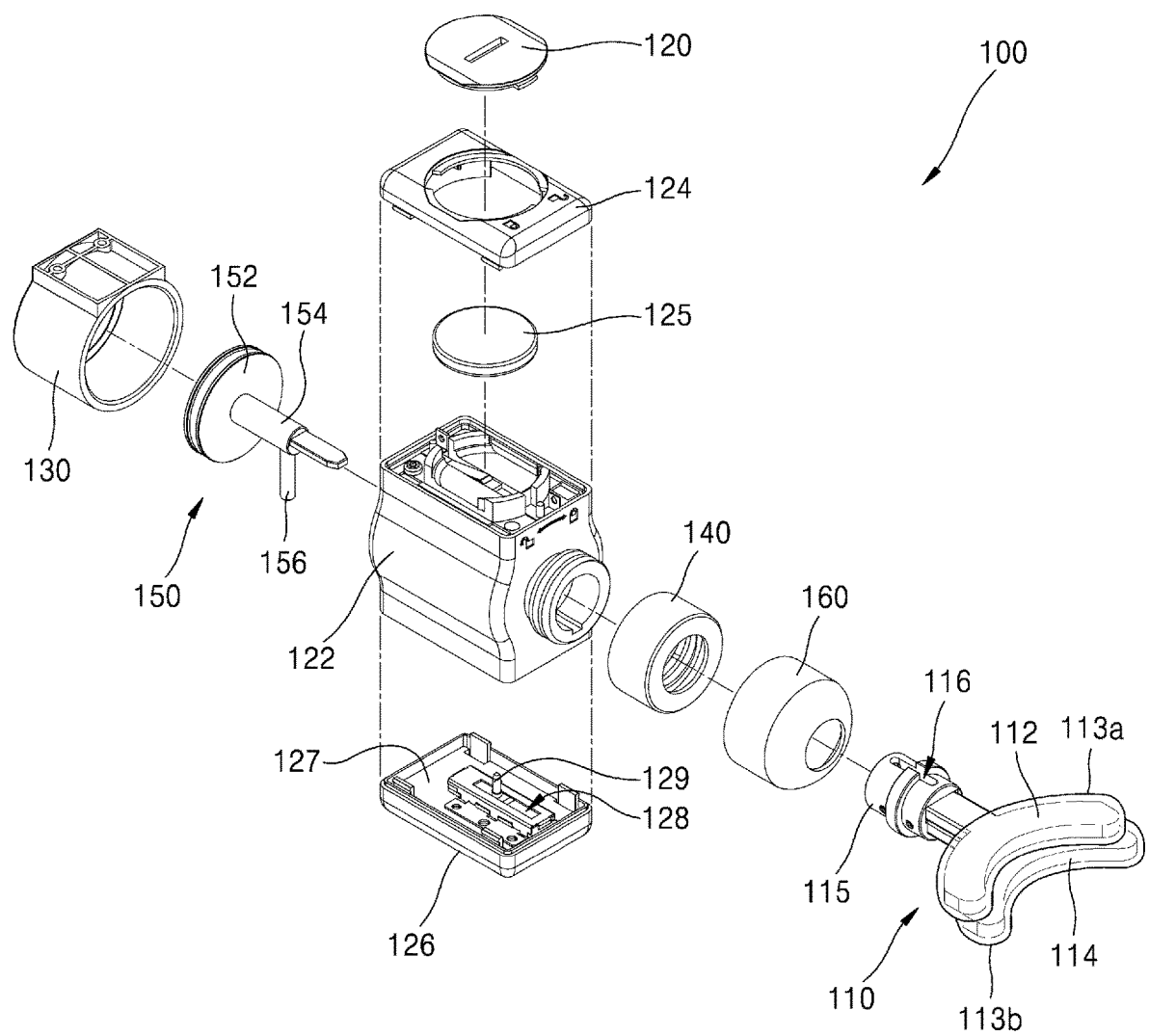
FIG. 2 is a schematic exploded perspective view of an example of a driving unit of FIG. 1.
Figure 3:
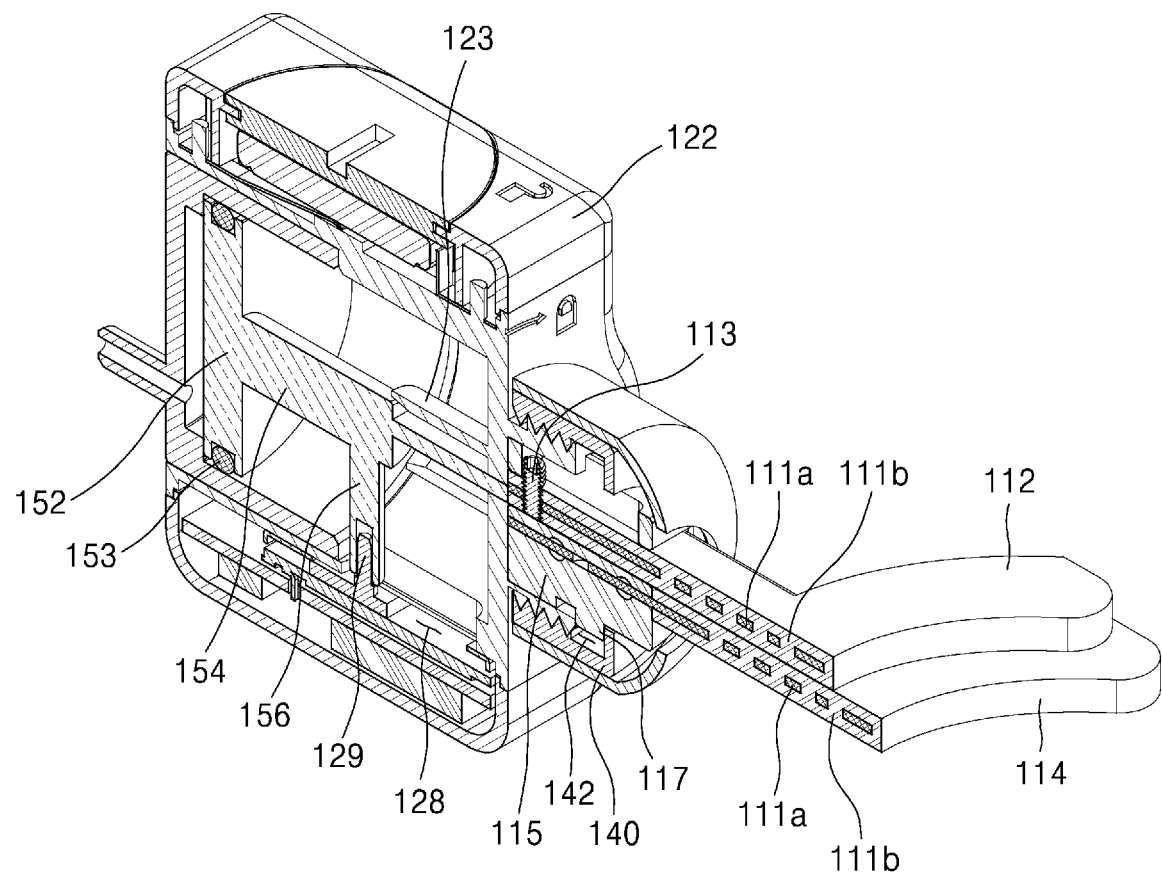
FIGS. 3 and 4 are schematic cross-sectional views of an example of a cross-section I-I' of FIG. 1.
Figure 4:
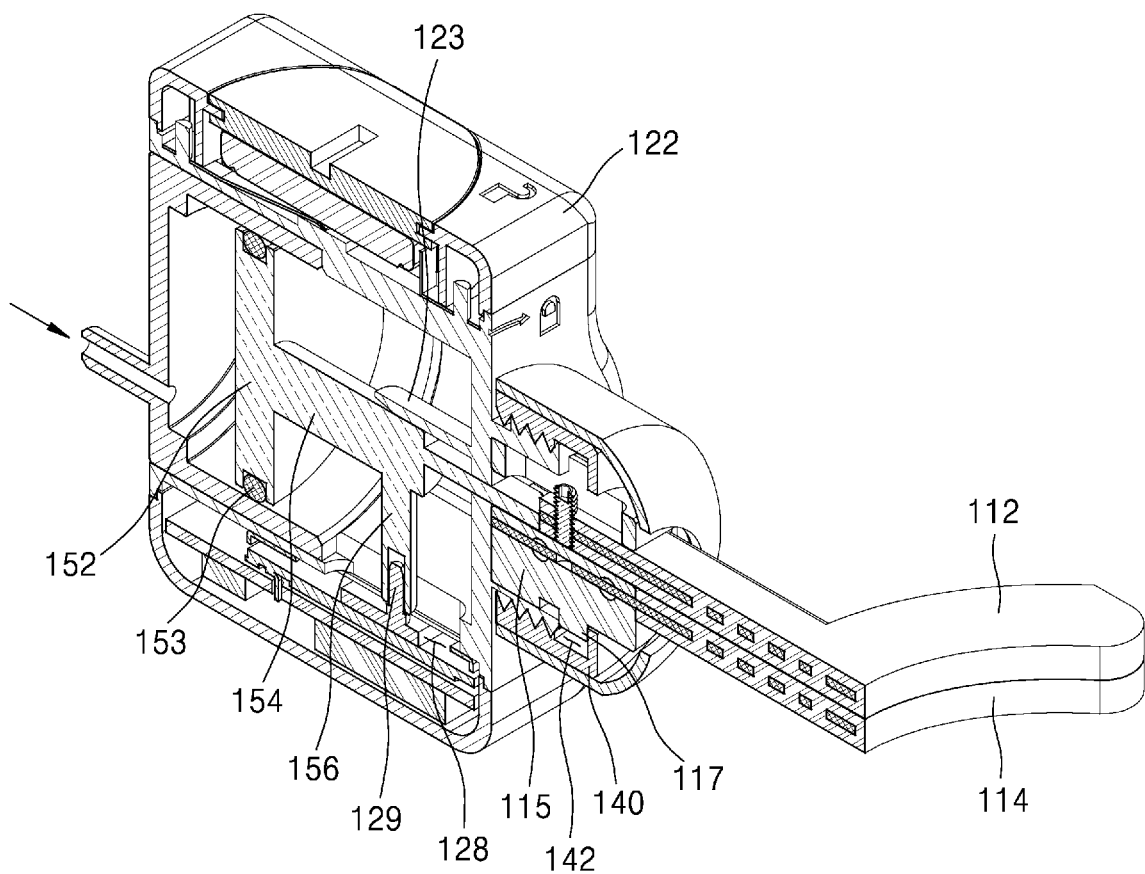
Figure 5:
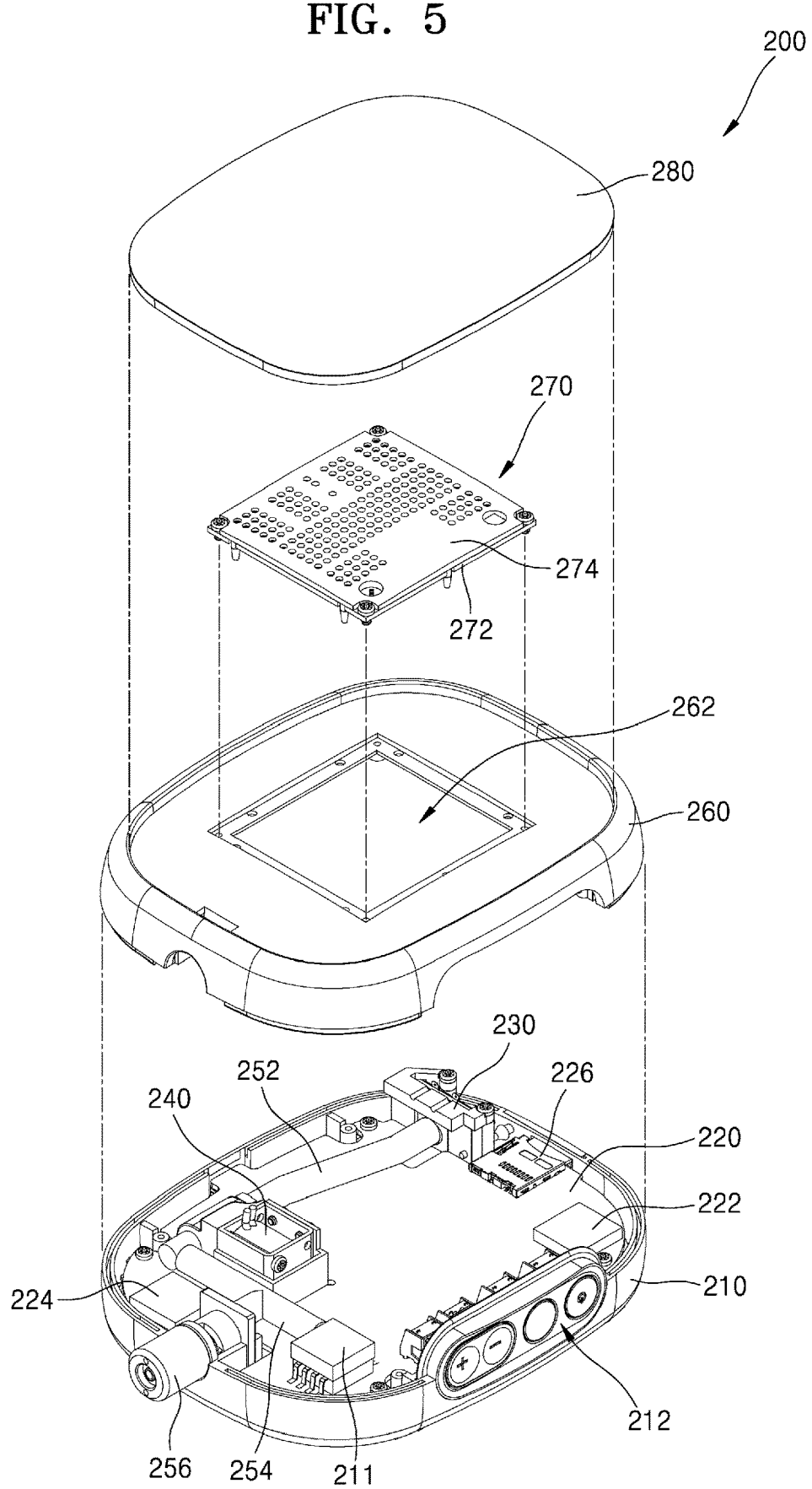
FIG. 5 is a schematic exploded perspective view of an example of a main body of FIG. 1.

FIG. 1 is a schematic perspective view of a mandibular advancement device according to an embodiment of the present disclosure, FIG. 2 is a schematic exploded perspective view of an example of a driving unit of FIG. 1, FIGS. 3 and 4 are schematic cross-sectional views of an example of a cross-section I-I' of FIG. 1, and FIG. 5 is a schematic exploded perspective view of an example of a main body of FIG. 1.

Hereinafter, a mandibular advancement device 10 according to an embodiment of the present disclosure will be described with reference to FIGS. 1 to 5. Meanwhile, in FIGS. 3 and 4, a first seating portion 113a and a second seating portion 113b are omitted.

Referring to FIGS. 1 to 5, the mandibular advancement device 10 according to an embodiment of the present disclosure may include a driving unit 100 including an intraoral device 110 located in the oral cavity of a user, a main body 200 that generates a driving force for driving the driving unit 100 and controls the operation of the driving unit 100, and a connection unit 300 that connects the driving unit 100 and the main body 200 to transmit the driving force generated by the main body 200 to the driving unit 100. In other words, since the driving unit 100 and the main body 200 are separated from each other, the weight of the driving unit 100 is reduced, thereby minimizing discomfort caused by wearing the mandibular advancement device 10.

The driving unit 100 may include a driving case 122 having an empty space therein, the intraoral device 110 located in the oral cavity of a user, a coupling unit 140 coupled to the front of the driving case 122 and having fixed thereto the intraoral device 110, and a rear cover 130 coupled to the rear of the driving case 122 and accommodating a piston 150 therein.

The intraoral device 110 may include the first seating portion 113a and the second seating portion 113b located in the oral cavity, a first frame 112 at least partially buried by the first seating portion 113a, a second frame 114 at least partially buried by the second seating portion 113b, and a fixing unit 115 coupled to the first frame 112 and the second frame 114. In other words, the first seating portion 113a may cover a portion of the first frame 112 located in the oral cavity of a user, and the second seating portion 113*b* may cover a portion of the second frame 114 located in the oral cavity of the user.

The first seating portion 113*a* and the second seating portion 113*b* are portions on which teeth of the user may be directly seated and may include a material liked an acrylic resin. Also, at least portions of the first seating portion 113*a* and the second seating portion 113*b* directly contacting teeth of the user may be coated with a soft material to prevent damage to the teeth and provide comfort when worn in the oral cavity.

The first seating portion 113*a* and the second seating portion 113*b* may be custom-made according to the teeth arrangement of a user. For example, the first seating portion 113*a* may be formed in a shape that allows upper teeth of a user to be inserted, and thus, when worn on the upper teeth, the first seating portion 113*a* may surround the upper teeth and be in close contact with the upper teeth. In the same regard, the second seating portion 113*b* may be custom-made according to the teeth arrangement of the user and may surround the lower teeth and be in close contact to the lower teeth when worn on the lower teeth. Meanwhile, at least one of the first seating portion 113*a* and the second seating portion 113*b* may include an oxygen saturation sensor. The oxygen saturation sensor may measure an oxygen saturation from lips of the user, for example, and transmit a result of the measurement to a sensing unit 127 described later.

The first frame 112 and the second frame 114 may include a material having rigidity, e.g., a metal, glass fiber, carbon fiber, etc. For example, the first frame 112 and the second frame 114 may be metal frames. In another example, as shown in FIG. 3, the first frame 112 and the second frame 114 may each include a support 111*a* having rigidity and a molding portion 111*b* surrounding the support 111*a*. Also, the support 111*a* may include a plurality of holes, and the molding portion 111*b* may be formed with excellent bonding strength by filling the holes. The support 111*a* may include a metal, glass fiber, carbon fiber, etc.

The first frame 112 and the second frame 114 are positioned to overlap each other, and the fixing unit 115 may be coupled to ends of the first frame 112 and the second frame 114. At this time, the first frame 112 may be coupled to the fixing unit 115 to be relatively movable with respect to the second frame 114.

In detail, the first frame 112 may include a protrusion 113 vertically protruding from a surface of the first frame 112 opposite to a surface of the first frame 112 facing the second frame 114, and the fixing unit 115 may include a guide groove 116 extending to a certain length in a first direction, wherein the protrusion 113 is inserted to the guide groove 116. For example, the protrusion 113 may be a screw coupled to the first frame 112. Therefore, due to the protrusion 113 and the guide groove 116, the first frame 112 is prevented from being separated from the fixing unit 115, and the first frame 112 may move back and forth for a distance corresponding to the length of the guide groove 116. On the other hand, the second frame 114 may be firmly fixed to the fixing unit 115.

The fixing unit 115 is coupled to the coupling unit 140, and the coupling unit 140 is coupled to the front of the driving case 122 again. For example, as shown in FIG. 3, the fixing unit 115 includes a fastening protrusion 117 protruding outward from the outer circumferential surface of the fixing unit 115, and the coupling unit 140 includes a fastening groove 142 coupled to the fastening protrusion 117. Also, for example, the coupling unit 140 and the front of the driving case 122 may be coupled to each other by screw threads. The fixing unit 115 as described above may be covered by a front cover 160.

On the other hand, the piston 150 may include a piston head 152 disposed inside the rear cover 130, a push arm 154 protruding from the center of the piston head 152 toward the fixing unit 115, and a fitting protrusion 156 protruding from the push arm 154 in a direction perpendicular to a direction in which the push arm 154 extends.

As will be described later, when a driving force is supplied from the main body 200, the piston 150 may move toward the fixing unit 115 by the driving force. For example, the driving force may be compressed air, and, in this case, an O-ring 153 for preventing air leakage may be located on the outer circumferential surface of the piston head 152. In another example, the piston head 152 may be covered with a rubber material.

When a driving force is applied to the piston 150, as shown in FIG. 4, the push arm 154 pushes the first frame 112 by the movement of the piston 150. On the other hand, as described above, the upper teeth of the user are seated on the first seating portion 113*a*, and the second frame 114 partially buried by the second seating portion 113*b* on which the lower teeth of the user are seated is fixed to the driving case 122 through the fixing unit 115 and the coupling unit 140. Also, the maxillary, in which the upper teeth are arranged, is fixed to the skull, whereas the mandible, in which the lower teeth are arranged, may be moved forward by the temporomandibular joint. Therefore, when the piston 150 pushes the first frame 112, the position of the first frame 112 is not changed substantially. Meanwhile, the driving case 122 and the second frame 114 move backward in a direction opposite to a direction in which the piston 150 moves according to the law of action and reaction, and thus the mandible of a user is advanced.

Meanwhile, the fitting protrusion 156 protruding in a direction perpendicular to the direction in which the push arm 154 extends may be coupled to a rod 129. The rod 129 may be disposed on a lower cover 126 coupled to the bottom surface of the driving case 122 and may be covered by a guide 128. In an embodiment, the guide 128 includes a hole extending in one direction, and the rod 129 protrudes to the outside of the guide 128 through the hole, and the guide 128 may cover the lower end of the rod 129 having a larger area than the hole. Therefore, when the piston 150 moves, the rod 129 may move together.

Meanwhile, as shown in FIGS. 3 and 4, a guide tube 123 into which the push arm 154 is inserted when the piston 150 is moved may be formed inside the driving case 122, whereby the push arm 154 is prevented from being tilted when the piston 150 is moved. Therefore, the push arm 154 may push the first frame 112 at a correct position.

The driving unit 100 may further include the sensing unit 127. For example, the sensing unit 127 may be located on the lower cover 126. However, the present disclosure is not limited thereto, and the position of the sensing unit 127 may vary. For example, the sensing unit 127 may be located in the driving case 122 or may be covered by an upper cover 124.

The sensing unit 127 may include a sensor capable of detecting biometric information of a user and a communication module capable of transmitting and receiving data to and from the main body 200. Also, the sensing unit 127 may receive an oxygen saturation measured by at least one of the first seating portion 113*a* and the second seating portion 113*b*.

The sensor may include at least one of a breathing sound sensor and a position sensor to detect biometric information for determining a sleep state of a user, e.g., a sleeping position, snoring, or sleep apnea. The breathing sound sensor may be an acoustic sensor capable of detecting a snoring sound, and the position sensor may be a sensor for detecting biometric information for determining a sleeping position of a user. As an example, the position sensor may include a 3-axis sensor. The 3-axis sensor is a sensor that detects changes in a yaw axis, a pitch axis, and a roll axis, and may include at least one of a gyro sensor, an acceleration sensor, and a tilt sensor.

Also, the driving unit 100 may include a distance sensor capable of detecting a moving distance of the piston 150. As described above, when the piston 150 moves, the rod 129 also moves. Here, a variable resistance may be connected to the rod 129, and the distance sensor may detect a potential difference generated by the movement of the rod 129 and transmit the potential difference to a control unit, which will be described later. The control unit may convert the potential difference into a distance by using an analog digital converter (ADC) to check position information regarding the piston 150. The distance sensor may be located in the sensing unit 127, for example.

Also, the driving unit 100 may include a sensor S capable of determining a breathing state of a user. The sensor S may include at least one of a temperature sensor and a pressure sensor. The temperature sensor may detect a change in the temperature of inhalation and exhalation during respiration of a user, and the pressure sensor may monitor a change in pressure during exhalation, and the changes may be transmitted to the sensing unit 127. Therefore, a breathing state of the user may be determined. When the mandibular advancement device 10 is worn, the sensor S as described above may be located at a location adjacent to the nose of the user, e.g., inside the upper end of the driving case 122.

The communication module may include protocols like Bluetooth, ZigBee, medical implant communication service (MISC), and near field communication (NFC).

The driving unit 100 may include a power supply unit 125 for supplying power to the sensing unit 127. The power supply unit 125 may include a replaceable or rechargeable battery. For example, the power supply unit 125 may be located in the upper portion of the driving case 122, and the upper cover 124 coupled to the upper portion of the driving case 122 may be disposed over the power supply unit 125. Also, an opening for replacing the power supply unit 125 may be formed in the upper cover 124, and the opening may be closed by a power cover 120 that may be opened and closed. However, the present disclosure is not limited thereto, and the position of the power supply unit 125 may be variously set.

As shown in FIG. 5, the main body 200 may include a first case 210, a main circuit board 220 seated on the first case 210, and a second case 260 coupled to the first case 210. In addition, a display unit 270 is located on the second case 260, and the display unit 270 may be covered by a protection member 280.

The main body 200 may include, in addition to the main circuit board 220, an input unit 212, a power generating unit 230, a valve 240, a pressure sensor 211, a first communication module 222, a second communication module 224, and a memory attachment unit 226.

The main circuit board 220 may include an integrated circuit (IC) chip to control the overall operation of the mandibular advancement device 10. In other words, in the present disclosure, it may be understood that the control unit refers to the main circuit board 220. The control unit may control the operation of the driving unit 100 by controlling the operations of the power generating unit 230 and the valve 240.

The input unit 212 may include an on/off switch of the main body 200 and buttons for selecting an operation module and adjusting operation strength. Here, selection of an operation module may refer to selection of whether to operate the mandibular advancement device 10 according to a pre-set program or manually.

Any unit for generating the driving force is applicable to the power generating unit 230. For example, the power generating unit 230 may be a pump that generates compressed air. For example, when a piezo pump is used as the power generating unit 230, it is possible to reduce the discomfort of a user due to operation noise, because the driving frequency thereof is in a region higher than the human audible frequency.

Air generated by the pump may be supplied to the connection unit 300 connected to the main body 200 via a first pipe 252, a second pipe 254, and an outlet 256. A rubber packing for sealing and an air filter may be arranged at the outlet 256. The rubber packing for sealing prevents air leakage from the junction between the outlet 256 and the connection unit 300, and the air filter may prevent penetration of foreign substances through the outlet 256 when the main body 200 is separated from the connection unit 300 for a reason like storage of the mandibular advancement device 10.

The connection unit 300 transfers the air supplied from the main body 200 to the driving unit 100. The connection unit 300 may include a material having a flexible property for the convenience of using the mandibular advancement device 10.

Meanwhile, the valve 240 capable of blocking the flow of air may be disposed between the first pipe 252 and the second pipe 254. As an example, the valve 240 may be a solenoid valve, but is not limited thereto. In addition, the pressure sensor 211 may measure the pressure of the air supplied to the driving unit 100.

When the power generating unit 230 is driven while the valve 240 is opened, the air generated by the power generating unit 230 is injected into the rear cover 130, and the piston 150 moves by the pressure of the air and pushes out the first frame 112. Here, since the position of the first frame 112 is not substantially changed as described above, the second frame 114 is moved in a direction opposite to a direction in which the piston 150 moves by the force of pushing the first frame 112, and thus the mandible of the user is advanced.

When the mandible is advanced as much as needed, the valve 240 may be closed and the driving of the power generating unit 230 may be stopped. Therefore, even when the power generating unit 230 is not continuously driven, the pressure of the air for moving the piston 150 may be maintained, and the inconvenience caused by noise generated when the power generating unit 230 is driven may be minimized.

On the other hand, when the control unit determines that it is necessary to adjust the position of the piston 150 based on a result sensed by the distance sensor of the sensing unit 127, the power generating unit 230 is first driven again to increase the internal pressure of the first pipe 252, the valve 240 is opened, and the position of the piston 150 is adjusted.

When only the valve 240 is simply opened without re-driving the power generating unit 230, the compressed air in the rear cover 130, the connection unit 300, and the second pipe 254 expands at once and the piston 150 is abruptly moved backward. However, when the power generating unit 230 is driven before the valve 240 is opened, a position change of the piston 150 may be minimized even when the valve 240 is opened, and the position of the piston 150 may be re-adjusted with the minimum driving of the power generating unit 230.

The first communication module 222 may communicate with a user terminal outside the main body 200. The user terminal may be a terminal for performing a function of controlling the mandibular advancement device 10 by using the biometric information received from the mandibular advancement device 10 or transmitting the biometric information to a server. For example, the user terminal may be a smart phone. The first communication module 222 may include protocols like Bluetooth, ZigBee, medical implant communication service (MISC), and near field communication (NFC).

The second communication module 224 may communicate with the sensing unit 127 and receive biometric information of a user sensed by the sensing unit 127. The second communication module 224 may include protocols like Bluetooth, ZigBee, medical implant communication service (MISC), and near field communication (NFC).

A computer-readable recording storage medium may be mounted in the memory attachment unit 226. For example, the computer-readable recording storage medium may be an SD card. The computer-readable recording storage medium may store sleep state information like biometric information of the user detected by the sensor 127, results of the operation of the mandibular advancement device 10, etc.

The display unit 270 is located on the second case 260 coupled to the first case 210. The display unit 270 may include an LED substrate 272 on which a plurality of LEDs are arranged and a plate 274 stacked on the LED substrate 272. The plate 274 may include a plurality of holes at positions corresponding to the plurality of LEDs, such that light beams emitted by the plurality of LEDs are transmitted therethrough. Also, the plate 274 may be an optical waveguide that allows light beams generated by the plurality of LEDs to reach the protection member 280 without being diffused.

Meanwhile, an opening 262 is formed in the second case 260, and the LED substrate 272 may be connected to the main circuit board 220 through the opening 262. The display unit 270 may visually represent the operation state of the mandibular advancement device 10. To this end, the protection member 280 covering the display unit 270 may include a transparent material.

Figure 6:
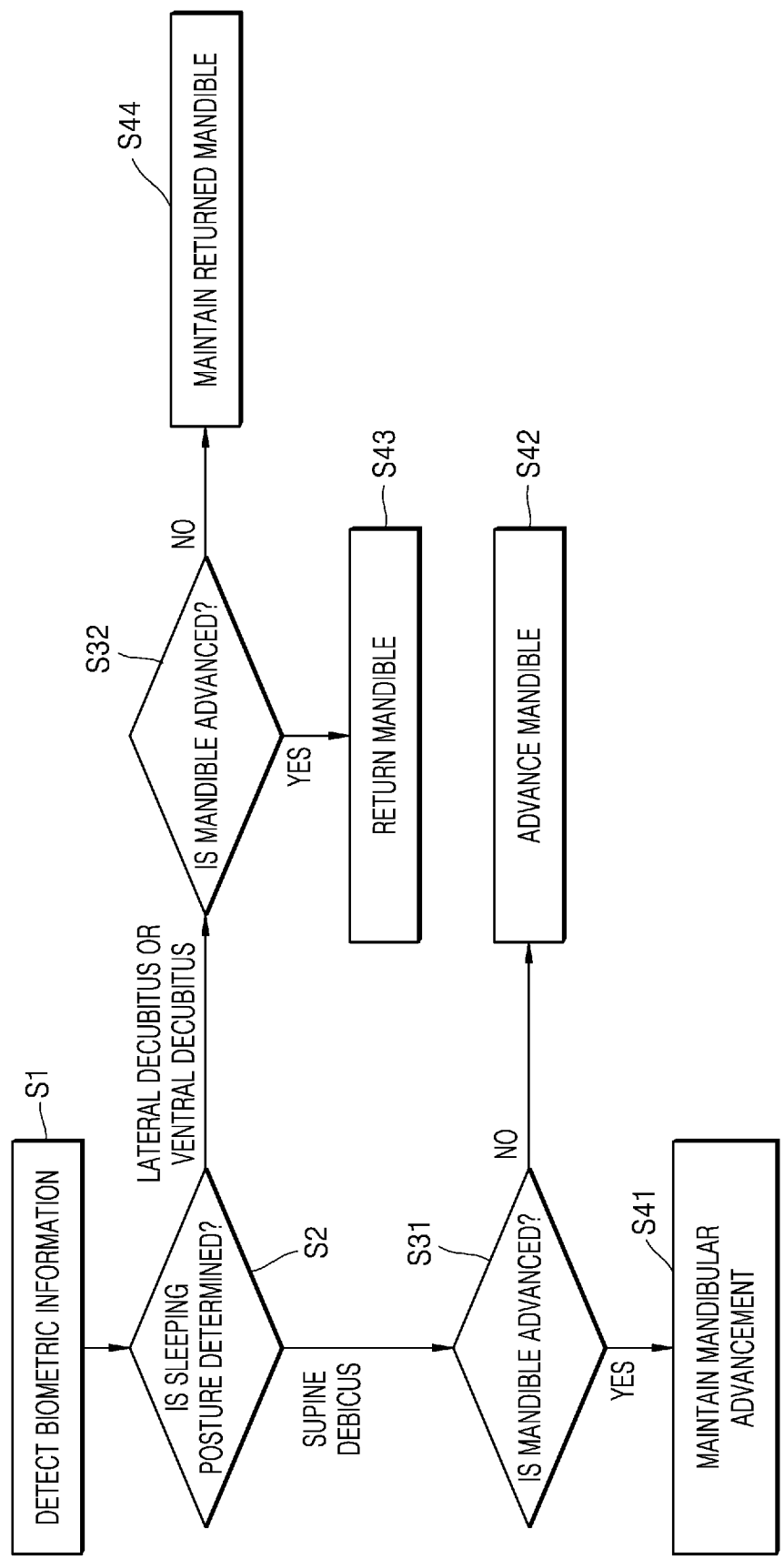
FIG. 6 is a flowchart schematically showing an example of a method of operating the mandibular battery device of FIG. 1.

FIG. 6 is a flowchart schematically showing an example of a method of operating the mandibular battery device of FIG. 1. Hereinafter, the method of operating the mandibular advance device will be described with reference to FIGS. 1 to 6 together.

First, when a user sleeps while the first seating portion 113a and the second seating portion 113b are seated in the oral cavity of the user, the sensing unit 127 detects biometric information, such as a breathing sound and a sleeping position of the user, (operation S1) and transmits the biometric information to the main body 200.

Data regarding the biometric information may be received by the second communication module 224 of the main body 200, and the control unit determines the sleeping position based on received data (operation S2). In detail, the control unit determines whether the user has actually entered sleep by using biometric information sensed by a breathing sound sensor, an oxygen saturation sensor, and/or the sensor S and determines the sleeping position of the user by using biometric information provided from a position sensor.

The control unit determines a supine position, a lateral position, a prone position, and a specific sleeping position (operation S2), and then determines whether the mandible is advanced (operations S31 and S32). The supine position is more likely to develop obstructive sleep apnea than the lateral position and the prone position.

For example, when the sleeping position is determined as the supine position and it is determined that the mandible is advanced as a result of determining whether the mandible is advanced (operation S31), the advancement of the mandible may be maintained (operation S41). On the other hand, when the sleeping position is determined as the supine position and it is determined that the mandible is not advanced as a result of determining whether the mandible is advanced (operation S31), the mandible may be advanced (operation S42) by the driving unit 100, the advancement of the mandible may be maintained unless the sleeping position of the user is changed to the lateral position or the prone position.

On the other hand, when the mandibular advancement device 10 operates, the second frame 114 may not always maintain an advanced state. Even when there is no change in the sleeping position for a certain period of time or longer, the mandible may be moved back at a certain time interval. The reason thereof is that, when the advancement of the mandible is maintained while the user is sleeping, fatigue and pain of the user may increase. The above-described certain time interval may be a time pre-set by the user. Alternatively, the certain time interval may be a result value derived by learning the sleep state of the user through the control unit or may be a value input in advance for a time period capable of minimizing the stress of the user. In other words, by moving the second frame 114 backward at a certain time interval while the user is sleeping, it is possible to help sound sleep of the user.

In another example, when the sleeping position is determined as the lateral position or the prone position and it is determined that the mandible is returned as a result of determining whether the mandible is advanced, the returned state of the mandible is maintained (operation S44). On the contrary, when the sleeping position is determined as the lateral position or the prone position and it is determined that the mandible is advanced as a result of determining whether the mandible is advanced, the valve 240 is opened to return the mandible (operation S43).

In other words, when the user wearing the mandibular advancement device 10 changes the sleeping position from the supine position to the lateral position or the prone position, the second frame 114 may return to its initial position. Therefore, when the user sleeps in the lateral position or the prone position, no compulsory force is applied, and thus the pain on the temporomandibular joint of the user may be relieved.

On the other hand, even when the sleeping position is the lateral position or the prone position, snoring may become severe for some users. In this case, the mandible may be advanced based on a snoring sound sensed by the sensing unit 127. In other words, priorities between the respective sensors may be set to determine whether the mandible is advanced, or it may be determined whether the mandible is advanced by comprehensively considering information sensed by the respective sensors. The operating conditions of the mandibular advancement device 10 may be pre-set according to a user's discretion, may be freely modified and used, or may be determined based on a learning model learned based on deep learning. Therefore, the operating conditions of the mandibular advancement device 10 may not be applied uniformly to everyone, but may be optimized and used for each individual.

Figure 7:
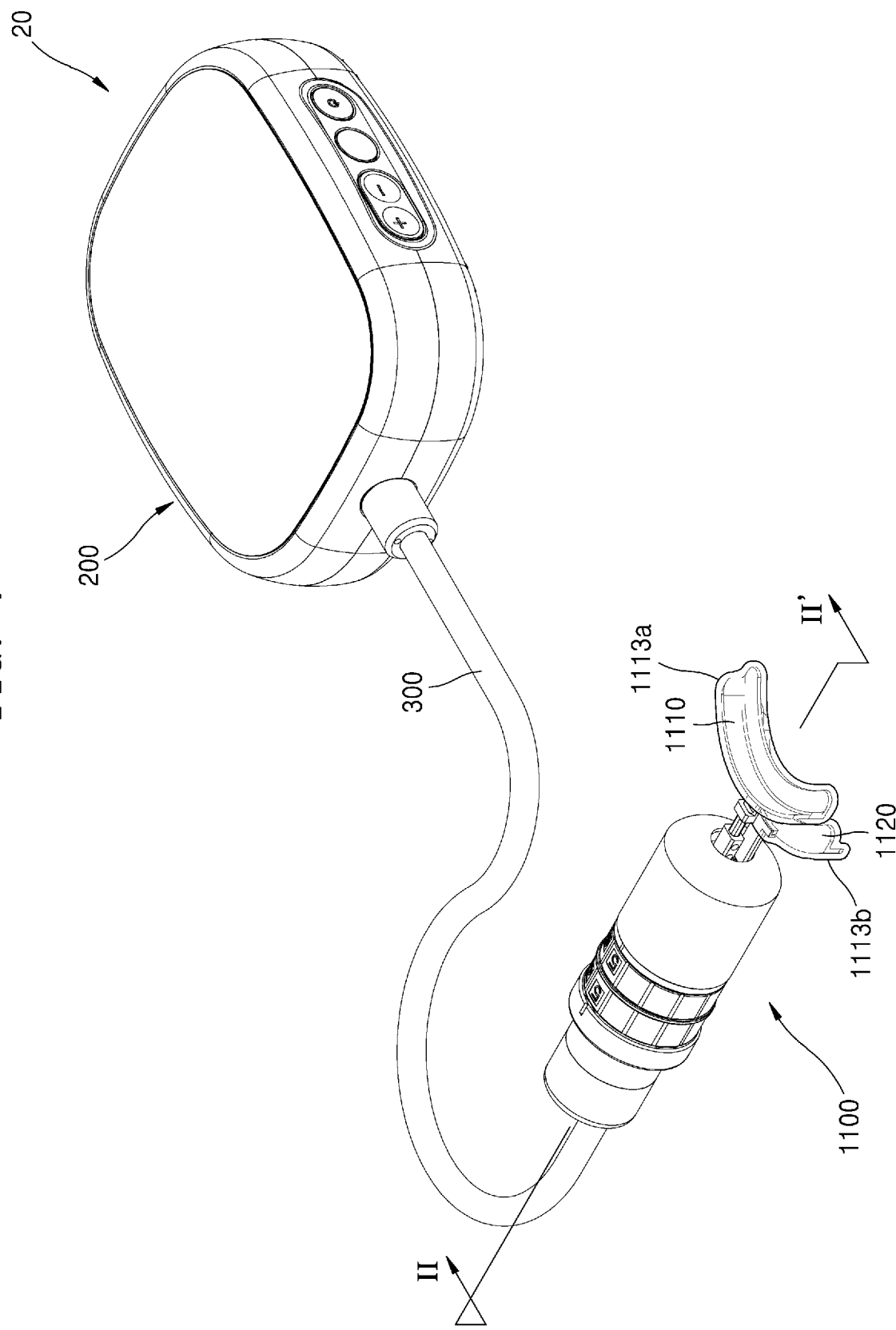
FIG. 7 is a schematic perspective view of a mandibular advancement device according to another embodiment of the present disclosure.
Figure 8:
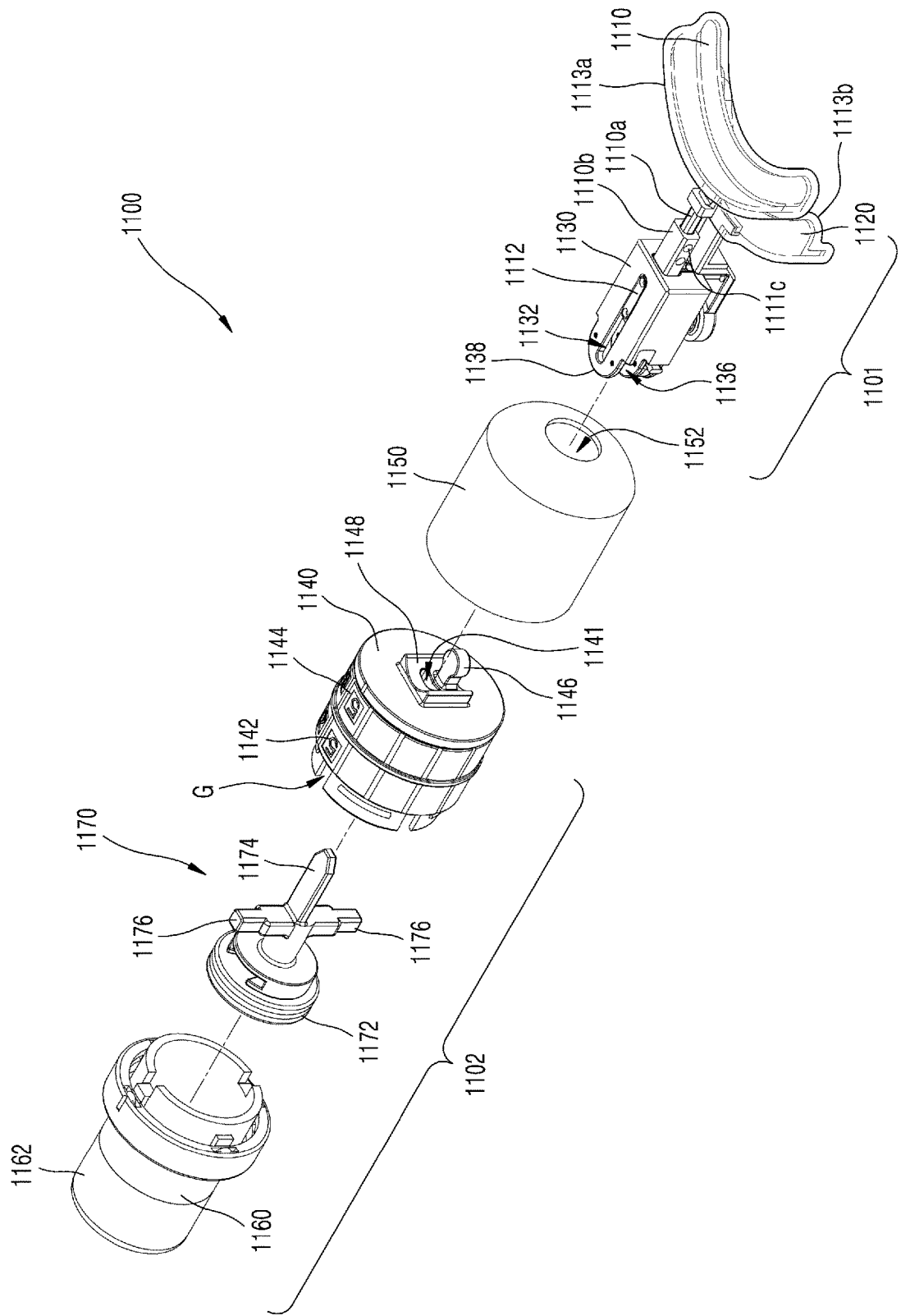
FIG. 8 is a schematic exploded perspective view of an example of a driving unit of FIG. 7.
Figure 9:
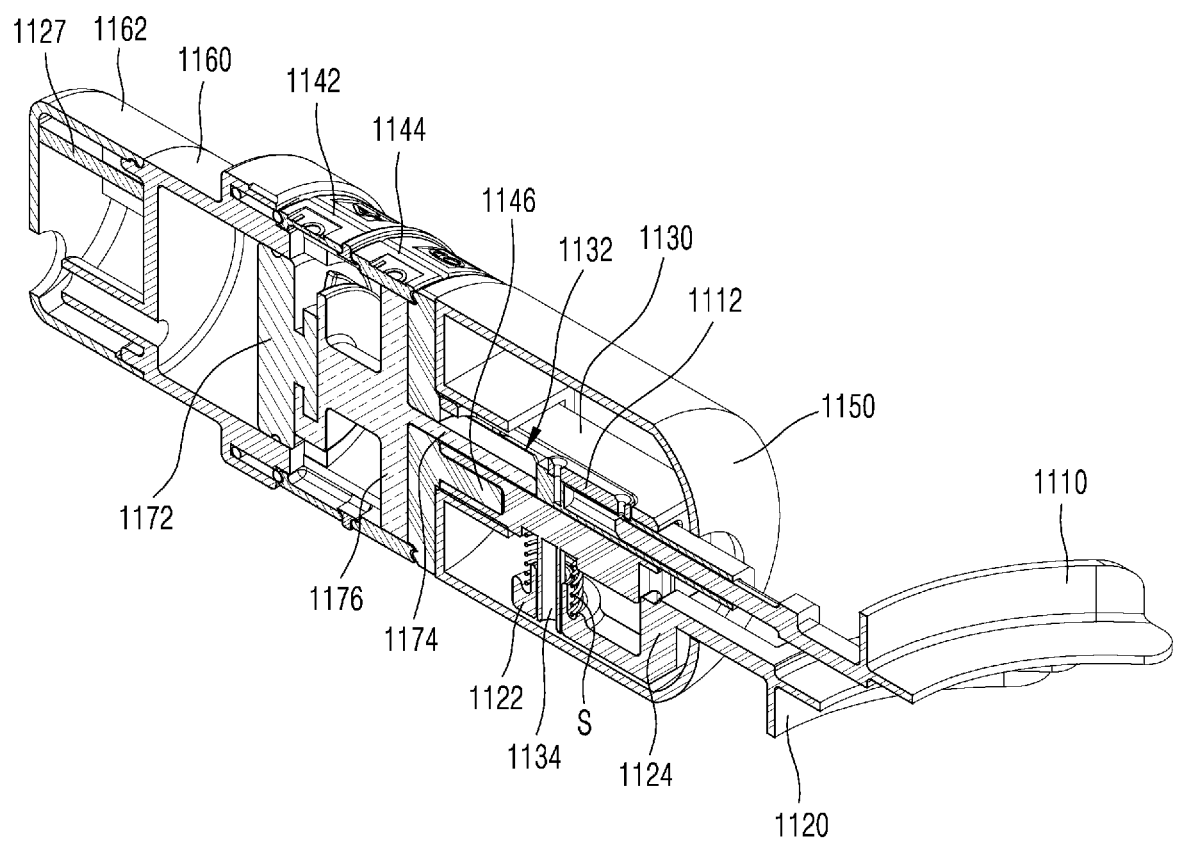
FIG. 9 is a schematic cross-sectional view of an example of a cross-section II-IT of FIG. 7.
Figure 10:
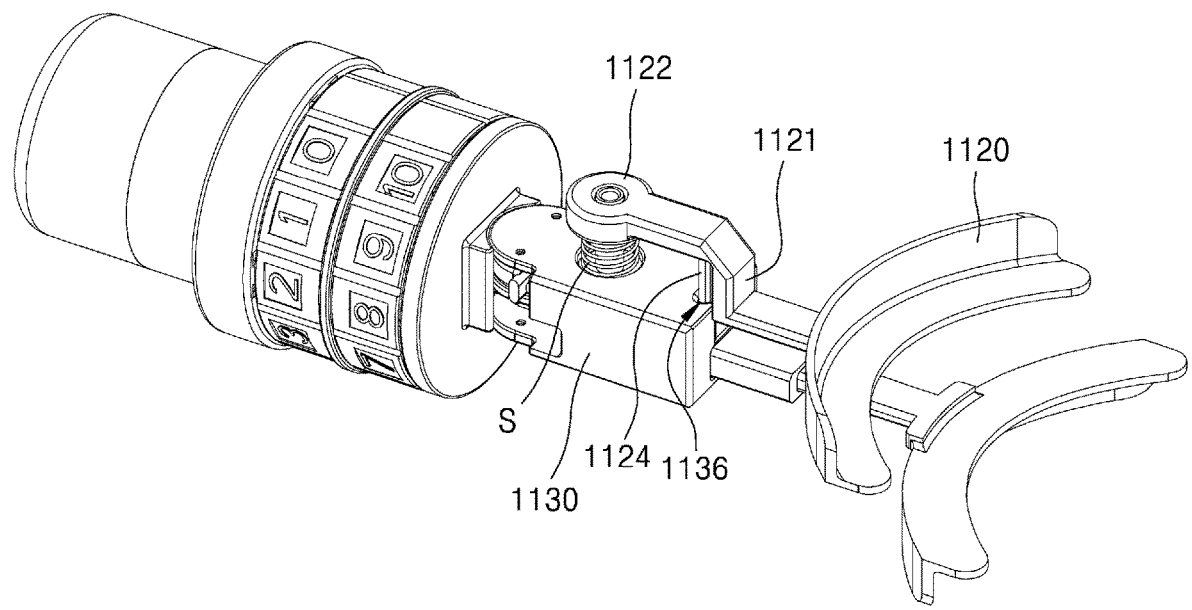
FIG. 10 is a schematic perspective view of a portion of the mandibular advancement device of FIG. 7.
Figure 11:
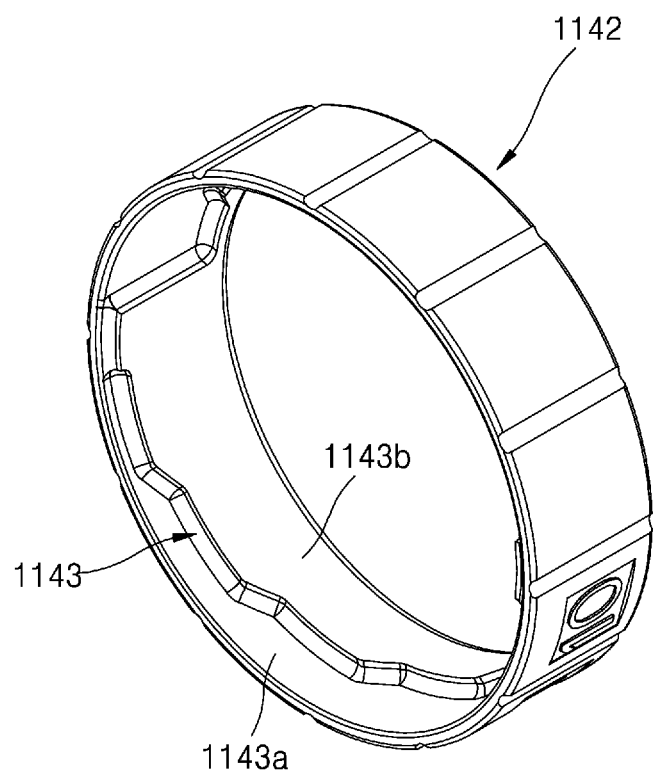
FIG. 11 is a schematic perspective view of an example of a first dial of the driving unit of FIG. 7.
Figure 12:
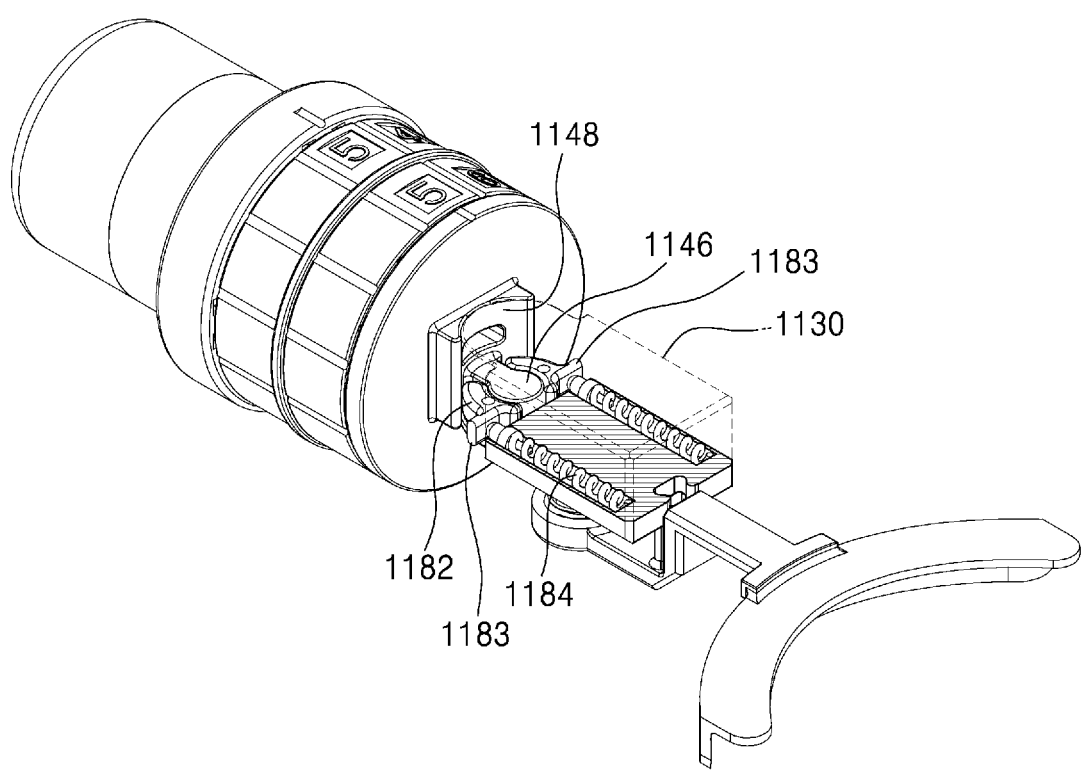
FIG. 12 is a schematic perspective view of a portion of the mandibular advancement device of FIG. 7.

FIG. 7 is a schematic perspective view of a mandibular advancement device according to another embodiment of the present disclosure, FIG. 8 is a schematic exploded perspective view of an example of a driving unit of FIG. 7, FIG. 9 is a schematic cross-sectional view of an example of a cross-section II-IT of FIG. 7, FIG. 10 is a schematic perspective view of a portion of the mandibular advancement device of FIG. 7, FIG. 11 is a schematic perspective view of an example of a first dial of the driving unit of FIG. 7, and FIG. 12 is a schematic perspective view of a portion of the mandibular advancement device of FIG. 7.

Hereinafter, a mandibular advancement device 20 according to another embodiment of the present disclosure will be described with reference to FIGS. 7 to 12. Meanwhile, a first seating portion 1113a and a second seating portion 1113b are shown in FIGS. 7 and 8 only for convenience of illustration. The mandibular advancement device 20 according to another embodiment of the present disclosure has the same components as the mandibular advancement device 10 according to an embodiment except for a driving unit 1100. For convenience of explanation, the same components are denoted by the same reference numerals, and descriptions identical to those given above will be omitted.

First, referring to FIGS. 7 to 12, the mandibular advancement device 20 according to another embodiment of the present disclosure may include the driving unit 1100, which includes a first frame 1110 and a second frame 1120 placed in the oral cavity of a user, the main body 200 that generates a driving force for driving the driving unit 1100 and controls the operation of the driving unit 1100, and the connection unit 300 that connects the driving unit 1100 to the main body 200 to transmit the driving force generated by the main body 200 to the driving unit 1100. In other words, since the driving unit 1100 and the main body 200 generating the driving force are separated from each other, the weight of the driving unit 1100 is reduced, thereby minimizing discomfort caused by wearing the mandibular advancement device 20.

The driving unit 1100 may include an intraoral device 1101 and a power transmission unit 1102 that are detachably coupled to each other.

The intraoral device 1101 may include the first seating portion 1113a and the second seating portion 1113b located in the oral cavity, the first frame 1110 at least partially buried by the first seating portion 1113a, the second frame 1120 at least partially buried by the second seating portion 1113b, and a guide 1130 coupled to the first frame 1110 and the second frame 1120. In other words, the first seating portion 1113a may cover a portion of the first frame 1110 located in the oral cavity of a user, and the second seating portion 1113b may cover a portion of the second frame 1120 located in the oral cavity of the user.

The first seating portion 1113a and the second seating portion 1113b are portions on which teeth of the user may be directly seated and may include a material liked an acrylic resin. Also, at least portions of the first seating portion 1113a and the second seating portion 1113b directly contacting teeth of the user may be coated with a soft material to prevent damage to the teeth and provide comfort when worn in the oral cavity.

The first seating portion 1113a and the second seating portion 1113b may be custom-made according to the teeth arrangement of a user. For example, the first seating portion 1113a may be formed in a shape that allows upper teeth of a user to be inserted, and thus, when worn on the upper teeth, the first seating portion 113a may surround the upper teeth and be in close contact with the upper teeth. In the same regard, the second seating portion 1113b may be custom-made according to the teeth arrangement of the user and may surround the lower teeth and be in close contact to the lower teeth when worn on the lower teeth. Meanwhile, at least one of the first seating portion 1113a and the second seating portion 1113b may include an oxygen saturation sensor. The oxygen saturation sensor may measure an oxygen saturation from lips of the user, for example, and transmit a result of the measurement to a sensing unit 1127 described later.

The first frame 1110 and the second frame 1120 may include a material having rigidity, e.g., a metal, glass fiber, carbon fiber, etc. For example, the first frame 1110 and the second frame 1120 may be metal frames. In another example, the first frame 1110 and the second frame 1120 may each include a support having rigidity and a molding portion surrounding the support. The support may include a metal, glass fiber, carbon fiber, etc. Also, the support may include a plurality of holes, and the molding portion may be formed with excellent bonding strength by filling the holes.

The first frame 1110 and the second frame 1120 may be positioned, such that at least regions thereof located in the oral cavity overlap each other, and may be fastened to the guide 1130. In this case, the first frame 1110 may be coupled to the guide 1130 to be relatively movable with respect to the second frame 1120 in a first direction. Here, the first direction is a direction parallel to a direction in which a piston 1170, which will be described later, moves.

In detail, the first frame 1110 includes a knob 1112 whose end is inserted into the guide 1130 and vertically protrudes from a surface of the first frame 1110 opposite to a surface of the first frame 1110 facing the second frame 1120. Also, the guide 1130 includes a guide hole 1132 extending in one direction on the top surface of the guide 1130, which is a surface facing the first frame 1110, and the knob 1112 may be inserted into the guide hole 1132. Therefore, the first frame 1110 is prevented from being separated from the guide 1130, and the first frame 1110 may move forward and backward in the first direction for a distance corresponding to the length of the guide hole 1132.

Meanwhile, the first frame 1110 may include a first part 1110a and a second part 1110b. For example, the second part 1110b may include the knob 1112, the first part 1110a may be inserted into the second part 1110b and pulled out from the second part 1110b, and the positions of the first part 1110a and the second part 1110b may be fixed by a fixing pin 1110c penetrating through side surfaces of the first part 1110a and the second part 1110b. Therefore, it is possible to finely adjust the position of the first seating portion 1113a for each user.

As shown in FIG. 10, the second frame 1120 has a shape bent along the front surface and the bottom surfaces of the guide 1130 facing the second frame 1120, and a bent portion 1121 facing the front surface of the guide 1130 may include a rail 1124 protruding toward the guide 1130. The rail 1124 may be vertically elongated from the bent portion 1121 of the second frame 1120. Also, a rail groove 1136 is formed on the front surface of the guide 1130 in a vertical direction, and the rail 1124 may be slidably fastened to the rail groove 1136. Therefore, the second frame 1120 is unable to move in the first direction, but may move in the vertical direction as the rail 1124 slides.

Also, the second frame 1120 includes a supporting unit 1122 facing the bottom surface of the guide 1130 and spaced apart from the guide 1130 by a certain distance, and the guide 1130 may include a rod 1134 that protrudes from the bottom surface of the guide 1130 and coupled to the supporting unit 1122. Also, a spring S may be located between the support 1122 and the guide 1130 around the rod 1134. Therefore, force is applied to the second frame 1120 in the vertical direction by the spring S, thereby moving the rail 1124 along the rail groove 1136. As a result, the first frame 1110 and the second frame 1120 may be spaced from each other in the vertical direction. Therefore, even when the jaw loses strength during sleep and the mouth opens, the first seating portion 1113a and the second seating portion 1113b maintain close contacts with the upper teeth and the lower teeth of the user, respectively, thereby preventing separation of the driving unit 1100 and improving the effect of using the mandibular advancement device 20.

The intraoral device 1101 as described above is coupled to the power transmission unit 1102 and may be covered by a front cover 1150. The front cover 1150 prevents the guide 1130 from being exposed to the outside and may include a hole 1152 at the front, such that only the first frame 1110 and the second frame 1120 located in the oral cavity protrude to the outside. The front cover 1150 may include, for example, silicon.

The power transmission unit 1102 may include a body 1140 coupled to the intraoral device 1101, a cylinder 1160 coupled to the rear of the body 1140, a rear cover 1162 coupled to the cylinder 1160, the piston 1170 disposed inside the cylinder 1160, and a first dial 1142 and a second dial 1144 arranged to surround the outer surface of the body 1140.

The body 1140 has an empty space therein, and may have, for example, a cylindrical shape. A fastening protrusion 1146 for coupling with the guide 1130 protrudes from the front surface of the body 1140, and an opening 1141 through which a piston rod 1174 may penetrate when the piston 1170 moves is formed. As described above, since the piston rod 1174 is inserted into the opening 1141, the piston rod 1174 may be prevented from being tilted when the piston 1170 moves.

The rear cover 1162 to which the connection unit 300 is connected is coupled to the cylinder 1160, driving force generated by the main body 200 is supplied to the cylinder 1160, and the piston 1170 may be moved toward the intraoral device 1101 by the driving force. For example, the driving force may be compressed air.

The piston 1170 may include a piston head 1172 disposed inside the cylinder 1160, the piston rod 1174 protruding from the center of the piston head 1172 toward the intraoral device 1101, and a plurality of support beams 1176 protruding from the piston rod 1174 in a direction perpendicular to a direction in which the piston rod 1174 extends. Here, the plurality means at least two. Although FIG. 8 shows an example in which a pair of support beams 1176 protrude from the piston rod 1174 in opposite directions and extend, the present disclosure is not limited thereto, and three or more support beams 1176 may be formed.

A sealing member for preventing air leakage may be located on the outer circumferential surface of the piston head 1172. For example, the sealing member may be an O-ring. In another example, the piston head 1172 may be covered with a rubber material.

Meanwhile, a plurality of grooves G are formed in the body 1140. The plurality of grooves G may be spaced apart from one another at a certain distance in the circumferential direction of the body 1140 and may extend from one end of the body 1140 in the lengthwise direction of the body 1140. The plurality of support beams 1176 may be positioned in the grooves G.

When a driving force is applied to the piston 1170, the piston rod 1174 passes through the opening 1141 and pushes the first frame 1110 by the movement of the piston 1170.

On the other hand, as described above, the first seating portion 1113a on which the upper teeth of the user are seated is formed on the first frame 1110 coupled to the guide 1130 to be movable in the first direction, and the second frame 1120 partially buried by the second seating portion 1113b on which the lower teeth of the user are seated is coupled to the guide 1130 to not to be movable in the first direction, and the guide 1130 is coupled to the power transmission unit 1102. Also, the maxillary, in which the upper teeth are arranged, is fixed to the skull, whereas the mandible, in which the lower teeth are arranged, may be moved forward by the temporomandibular joint.

Therefore, when the piston rod 1174 pushes the first frame 1110, the position of the first frame 1110 is not changed substantially. Meanwhile, the second frame 1120, the guide 1130, and the body 1140 move backward in a direction opposite to a direction in which the piston 1170 moves as a reaction of the pushing, and thus the mandible of the user is advanced.

Referring back to FIG. 8, a first dial 1142 and a second dial 1144 may be further arranged on the body 1140. Meanwhile, although it is described in the present disclosure that the power transmission unit 1102 includes the first dial 1142 and the second dial 1144, the present disclosure is not limited thereto, and the power transmission unit 1102 may include either one of the first dial 1142 and the second dial 1144 or may include three or more dials. Also, since the first dial 1142 and the second dial 1144 may have substantially the same shape, only the first dial 1142 will be described below.

As shown in FIG. 11, the first dial 1142 may have a cylindrical shape to surround the outer circumferential surface of the body 1140, and the inner side surface may include a first region 1143a and a second region 1143b having different heights from each other. A boundary 1143 between the first region 1143a and the second region 1143b may be formed, such that a distance from any one edge thereof gradually decreases along the circumference of the first dial 1142. For example, although FIG. 11 shows an example in which the boundary 1143 between the first region 1143a and the second region 1143b is formed in a step-like shape having a smooth curve, the present disclosure is not limited thereto, and the boundary 1143 may be formed in a straight line shape.

The thickness of the first region 1143a is smaller than the thickness of the second region 1143b, and the support beams 1176 coupled to the grooves G of the body 1140 may contact the first region 1143a. Therefore, when the first dial 1142 is rotated, the support beams 1176 are gradually pushed by the second region 1143b at the boundary 1143 between the first region 1143a and the second region 1143b and move in straight lines along the grooves G. As a result, the first frame 1110 may be advanced. In other words, before supplying a driving force to the power transmission unit 1102, relative positions of the first frame 1110 and the second frame 1120 may be set according to a user.

Moreover, since the position of the first frame 1110 may be adjusted by using the first dial 1142 and the second dial 1144, the intraoral device 1101 may be used even when the main body 200 malfunctions or only the driving unit 1100 is carried, and, as will be described later, even when the operation of the driving unit 1100 stops for a certain period in consideration of the fatigue of a user, advancement of the mandible may be maintained to secure the minimum airway, thereby maintaining the function of preventing apnea.

Referring back to FIG. 8, the body 1140 includes the fastening protrusion 1146 protruding from the front surface to be coupled with the guide 1130, and a seating portion 1136 into which the fastening protrusion 1146 may be inserted is formed at the guide 1130. The seating portion 1136 is located between the top surface and the bottom surface of the guide 1130.

On the other hand, an end portion 1138 of the guide 1130 facing toward the power transmission unit 1102 may have a round shape, and a priming surface 1148 from which a region including the fastening protrusion 1146 protrudes is formed on the front surface of the body 1140, wherein the priming surface 1148 may have a concavely round shape in correspondence to the end portion 1138 of the guide 1130.

Also, the fastening protrusion 1146 may include an end portion circular when viewed from above, and the guide unit 1130 may include a pair of latches 1182 surrounding the end portion of the fastening protrusion 1146 from both sides. Here, the pair of latches 1182 may receive a force by a pair of latch springs 1184 buried in the guide 1130, respectively, move and closed along side surfaces of the fastening protrusion 1146, and fastened to the fastening protrusion 1146.

Meanwhile, the pair of latches 1182 may have rounded outer surfaces in correspondence to the shape of the priming surface 1148 and may include locking protrusions 1183 protruding outward from ends of the outer surfaces. Therefore, when the latch springs 1184 are compressed by pressing the locking protrusions 1183 of the pair of latches 1182, the latches 1182 are opened from each other, and thus the fastening with the fastening protrusion 1146 may be released. In other words, since the intraoral device 1101 may be easily separated from the power transmission unit 1102, the first seating portion 1113a and the second seating portion 1113b located in the oral cavity may be easily cleaned.

Also, when the head of the user sleeping while wearing the intraoral device 1101 is significantly rotated as the sleeping position of the user is changed to the prone position, a force may be applied to a side of the driving unit 1100 and the teeth of the user holding the intraoral device 1101 may be damaged. However, according to the present disclosure, since the priming surface 1148 protruding outward has a concavely round shape, when a force is applied to a side of the driving unit 1100, any one of the locking protrusions 1183 is pressed by the priming surface 1148, and thus any one of the latch springs 1184 is compressed. At this time, when the latch spring 1184 is compressed by a certain force or more, the pair of latches 1182 are sufficiently opened, and thus the power transmission unit 1102 may be separated from the intraoral device 1101 to prevent the teeth of the user from being damaged.

The driving unit 1100 may further include the sensing unit 1127. For example, as shown in FIG. 9, the sensing unit 1127 may be located in a rear cover 126. However, the present disclosure is not limited thereto, and the position of the sensing unit 1127 may vary. For example, the sensing unit 1127 may be located in the front cover 1150.

The sensing unit 1127 may include a sensor capable of detecting biometric information of a user and a communication module capable of transmitting and receiving data to and from the main body 200. Also, the sensing unit 1127 may receive an oxygen saturation measured by at least one of the first seating portion 1113a and the second seating portion 1113b.

Also, the driving unit 1100 may include a sensor 1151 capable of determining a breathing state of a user. The sensor 1151 may include at least one of a temperature sensor and a pressure sensor. The temperature sensor may detect a change in the temperature of inhalation and exhalation during respiration of a user, and the pressure sensor may monitor a change in pressure during exhalation, and the changes may be transmitted to the sensing unit 1127. Therefore, a breathing state of the user may be determined. When the mandibular advancement device 20 is worn, the sensor 1151 as described above may be located at a location adjacent to the nose of the user, e.g., inside the upper end of the front cover 1150 as shown in FIG. 9.

As shown in FIG. 7, the main body 200 may include a first case 210, a main circuit board 220 seated on the first case 210, and a second case 260 coupled to the first case 210. In addition, a display unit 270 is located on the second case 260, and the display unit 270 may be covered by a protection member 280.

The connection unit 300 transfers the air supplied from the main body 200 to the driving unit 100. The connection unit 300 may include a material having a flexible property for the convenience of using the mandibular advancement device 10.

Figure 13:
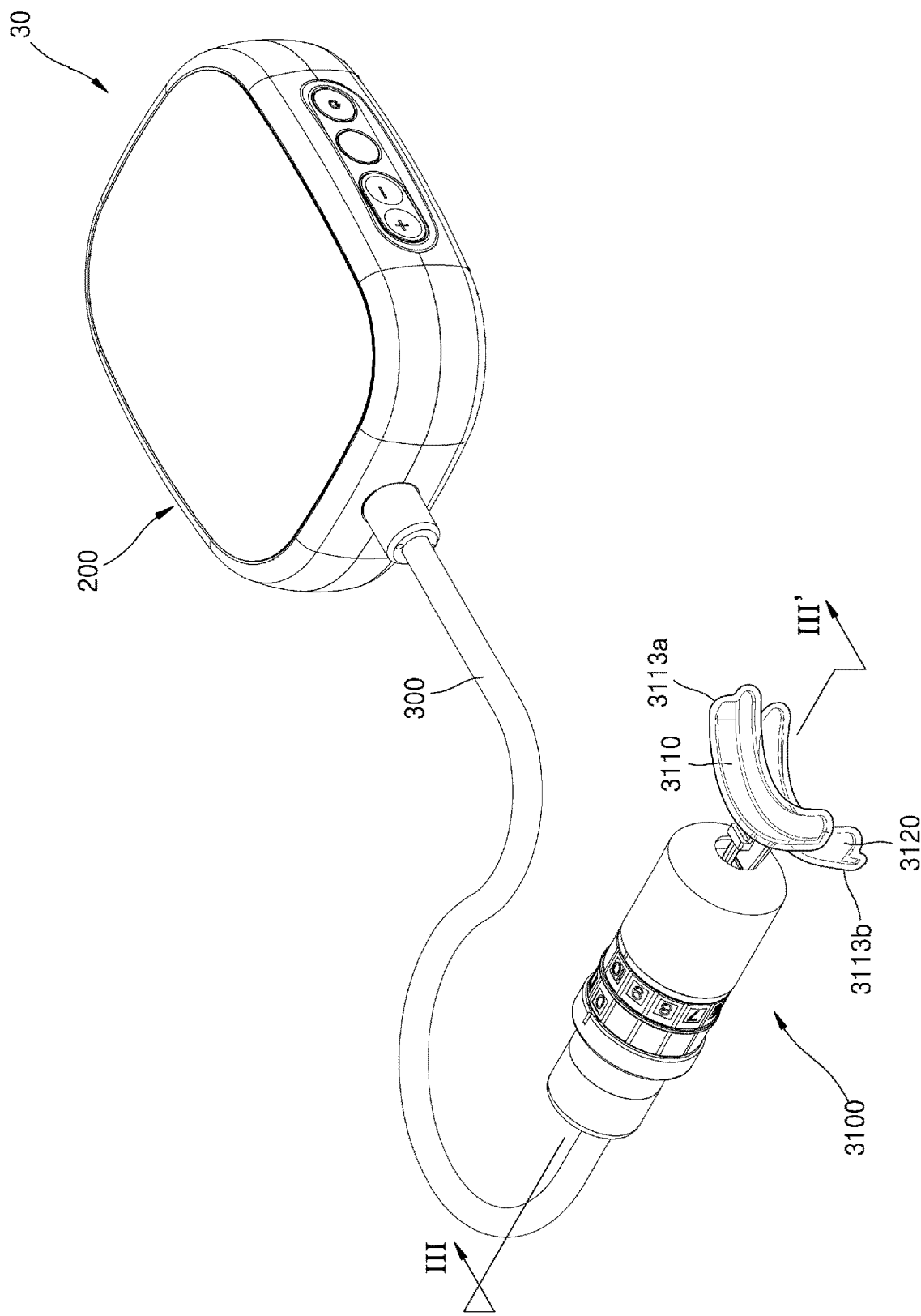
FIG. 13 is a schematic perspective view of a mandibular advancement device according to another embodiment of the present disclosure.
Figure 14:
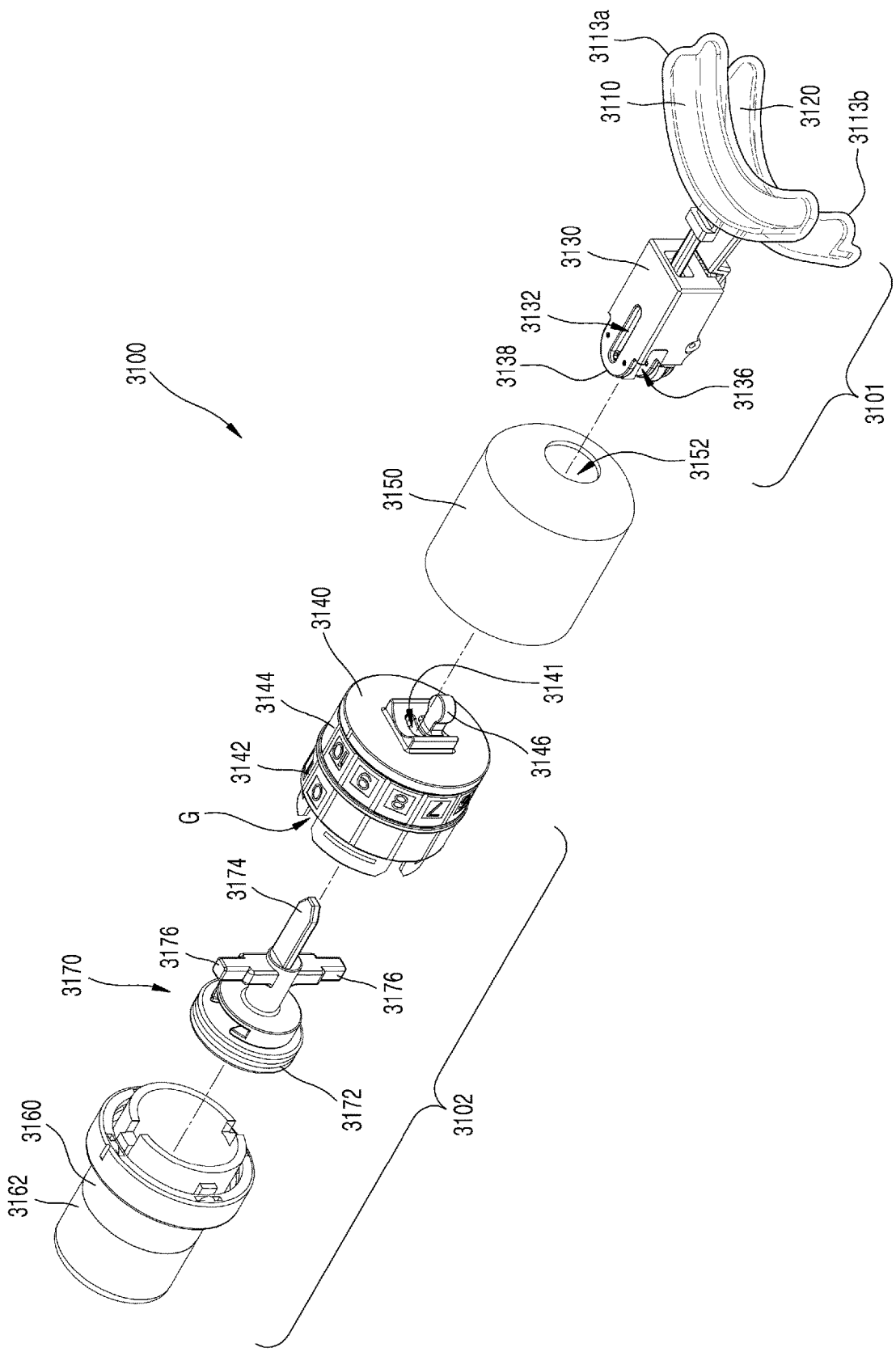
FIG. 14 is a schematic exploded perspective view of an example of a driving unit of FIG. 13.
Figure 15:
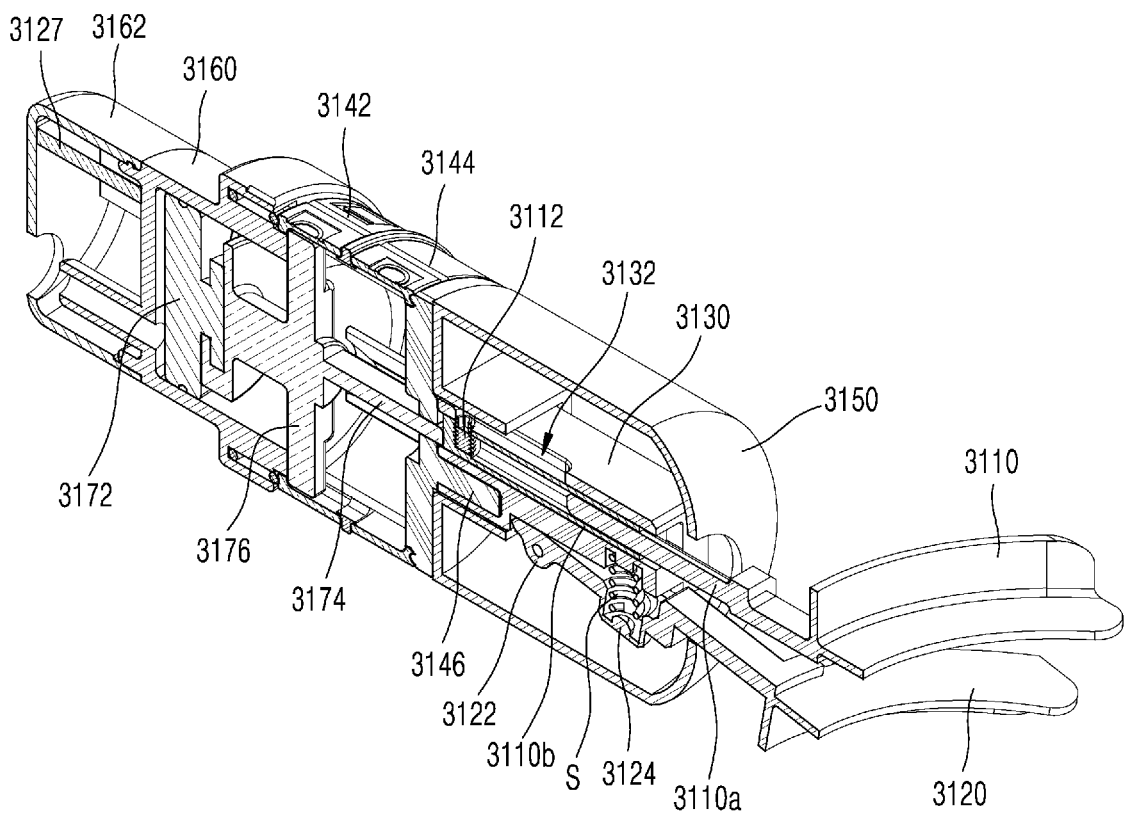
FIG. 15 is a schematic cross-sectional view of an example of a cross-section III-III' of FIG. 13.
Figure 16:
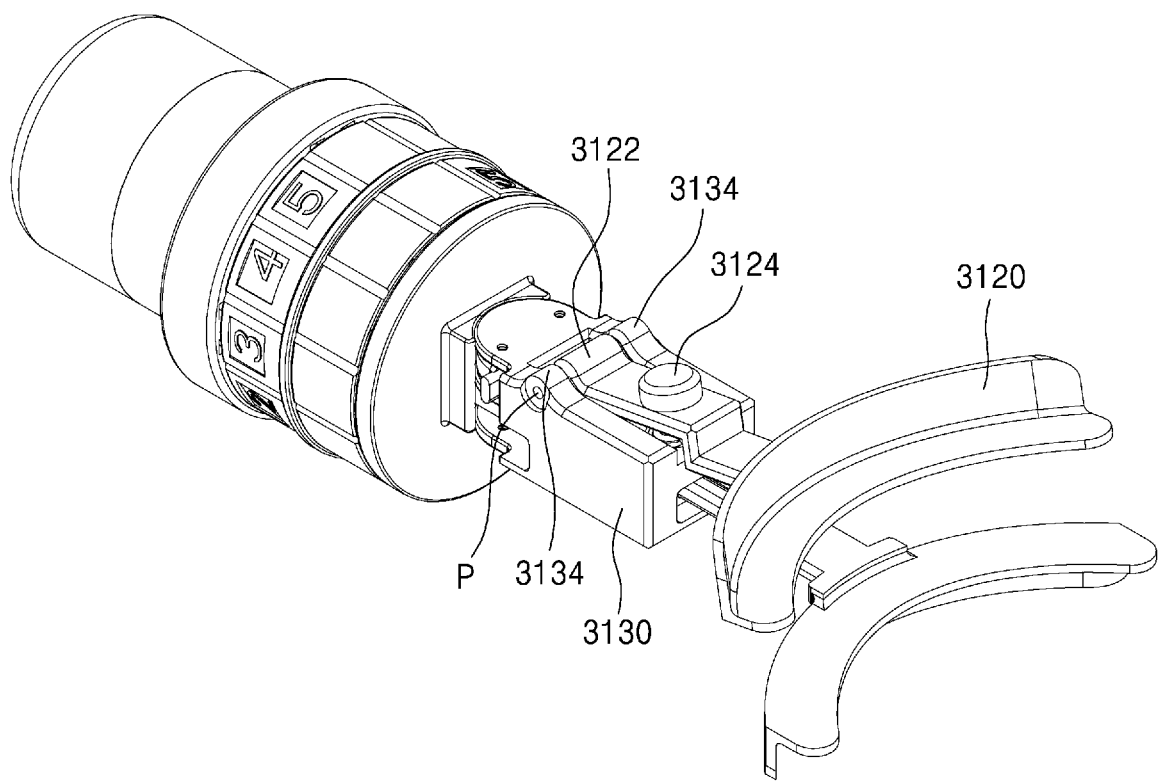
FIG. 16 is a schematic perspective view of a portion of the mandibular advancement device of FIG. 13.
Figure 17:
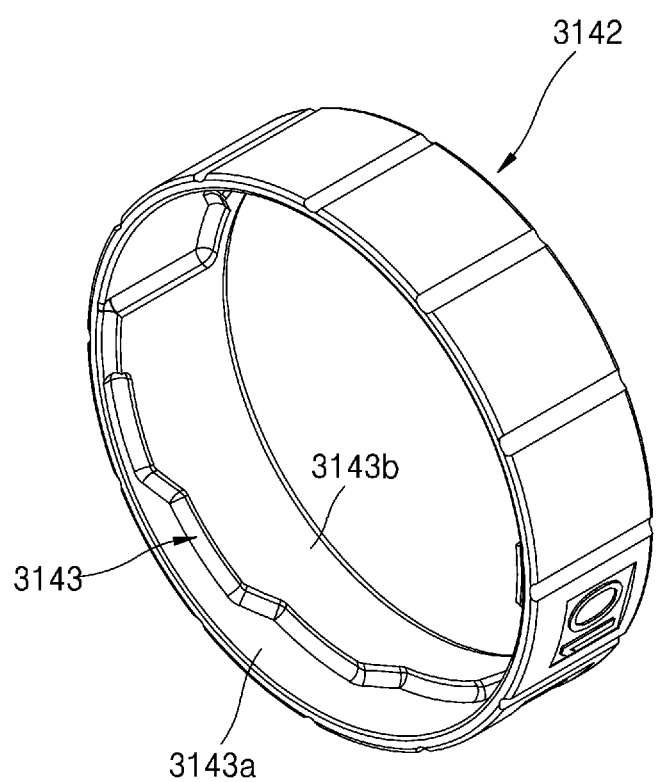
FIG. 17 is a schematic perspective view of an example of a first dial of the driving unit of FIG. 13.
Figure 18:
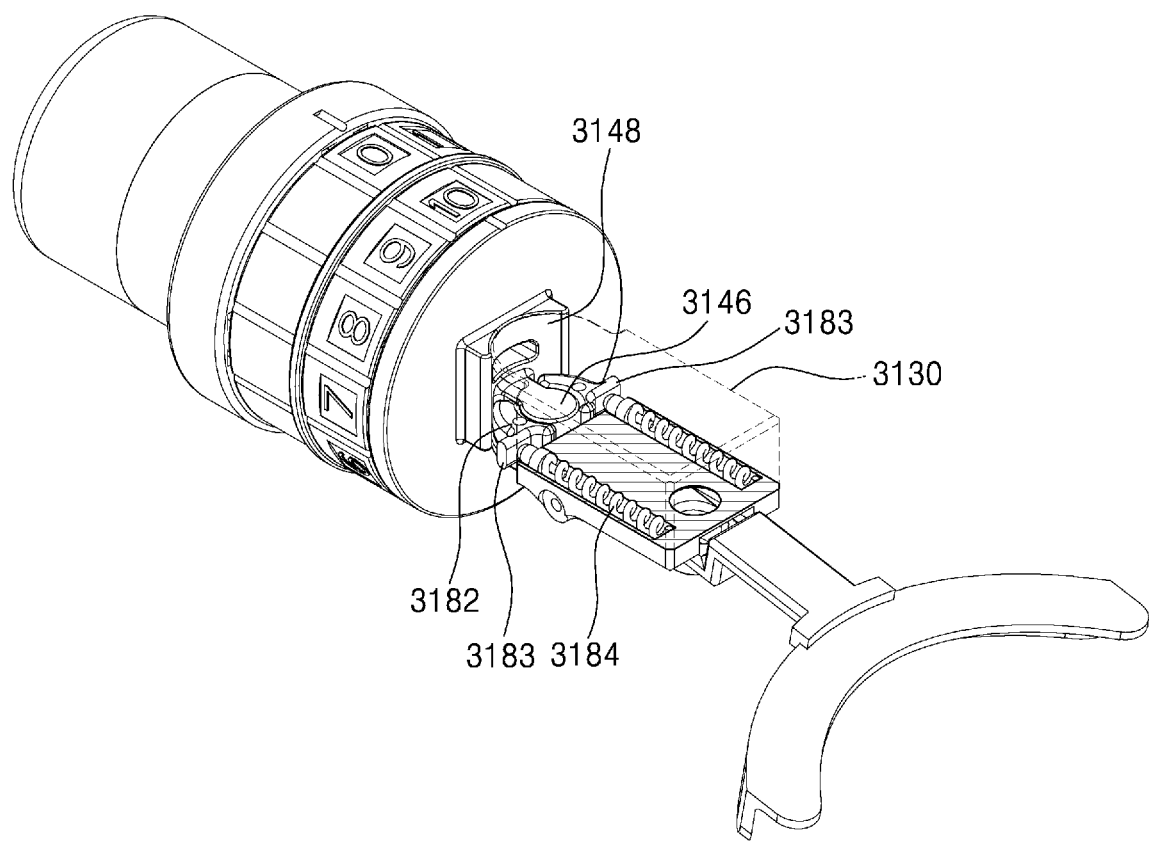
FIG. 18 is a schematic perspective view of a portion of the mandibular advancement device of FIG. 13.

FIG. 13 is a schematic perspective view of a mandibular advancement device according to another embodiment of the present disclosure, FIG. 14 is a schematic exploded perspective view of an example of a driving unit of FIG. 13, FIG. 15 is a schematic cross-sectional view of an example of a cross-section III-III' of FIG. 13, FIG. 16 is a schematic perspective view of a portion of the mandibular advancement device of FIG. 13, FIG. 17 is a schematic perspective view of an example of a first dial of the driving unit of FIG. 13, and FIG. 18 is a schematic perspective view of a portion of the mandibular advancement device of FIG. 13.

Hereinafter, a mandibular advancement device 30 according to another embodiment of the present disclosure will be described with reference to FIGS. 13 to 18. Meanwhile, a first seating portion 3113a and a second seating portion 3113b are shown in FIGS. 13 and 14 only for convenience of illustration. The mandibular advancement device 30 according to another embodiment of the present disclosure has the same components as the mandibular advancement device 10 according to an embodiment except for a driving unit 3100. For convenience of explanation, the same components are denoted by the same reference numerals, and descriptions identical to those given above will be omitted.

First, referring to FIGS. 13 to 18, the mandibular advancement device 30 according to another embodiment of the present disclosure may include the driving unit 3100, which includes a first frame 3110 and a second frame 3120 placed in the oral cavity of a user, the main body 200 that generates a driving force for driving the driving unit 3100 and controls the operation of the driving unit 3100, and the connection unit 300 that connects the driving unit 3100 to the main body 200 to transmit the driving force generated by the main body 200 to the driving unit 3100. In other words, since the driving unit 3100 and the main body 200 generating the driving force are separated from each other, the weight of the driving unit 3100 is reduced, thereby minimizing discomfort caused by wearing the mandibular advancement device 30.

As shown in FIG. 14, the driving unit 3100 may include an intraoral device 3101 and a power transmission unit 3102 that are detachably coupled to each other.

The intraoral device 3101 may include the first seating portion 3113a and the second seating portion 3113b located in the oral cavity, the first frame 3110 at least partially buried by the first seating portion 3113a, the second frame 3120 at least partially buried by the second seating portion 3113b, and a guide 3130 coupled to the first frame 3110 and the second frame 3120. In other words, the first seating portion 3113a may cover a portion of the first frame 3110 located in the oral cavity of a user, and the second seating portion 3113b may cover a portion of the second frame 3120 located in the oral cavity of the user.

The first seating portion 3113a and the second seating portion 3113b are portions on which teeth of the user may be directly seated and may include a material liked an acrylic resin. Also, at least portions of the first seating portion 3113a and the second seating portion 3113b directly contacting teeth of the user may be coated with a soft material to prevent damage to the teeth and provide comfort when worn in the oral cavity.

The first seating portion 3113a and the second seating portion 3113b may be custom-made according to the teeth arrangement of a user. For example, the first seating portion 3113a may be formed in a shape that allows upper teeth of a user to be inserted, and thus, when worn on the upper teeth, the first seating portion 113a may surround the upper teeth and be in close contact with the upper teeth. In the same regard, the second seating portion 3113b may be custom-made according to the teeth arrangement of the user and may surround the lower teeth and be in close contact to the lower teeth when worn on the lower teeth. Meanwhile, at least one of the first seating portion 3113a and the second seating portion 3113b may include an oxygen saturation sensor. The oxygen saturation sensor may measure an oxygen saturation from lips of the user, for example, and transmit a result of the measurement to a sensing unit 3127 described later.

The first frame 3110 and the second frame 3120 may include a material having rigidity, e.g., a metal, glass fiber, carbon fiber, etc. For example, the first frame 3110 and the second frame 3120 may be metal frames. In another example, the first frame 3110 and the second frame 3120 may each include a support having rigidity and a molding portion surrounding the support. The support may include a metal, glass fiber, carbon fiber, etc. Also, the support may include a plurality of holes, and the molding portion may be formed with excellent bonding strength by filling the holes.

The first frame 3110 and the second frame 3120 may be positioned, such that at least regions thereof located in the oral cavity overlap each other, and may be fastened to the guide 3130. In this case, the first frame 3110 may be coupled to the guide 3130 to be relatively movable with respect to the second frame 3120 in a first direction. Here, the first direction is a direction parallel to a direction in which a piston 3170, which will be described later, moves.

In detail, the first frame 3110 includes a protrusion 3112 whose end is inserted into the guide 3130 and vertically protrudes from a surface of the first frame 3110 opposite to a surface of the first frame 3110 facing the second frame 3120. Also, the guide 3130 includes a guide hole 3132 extending in one direction on the top surface of the guide 3130, which is a surface facing the first frame 3110, and the protrusion 3112 may be inserted into the guide hole 3132. Therefore, the first frame 3110 is prevented from being separated from the guide 3130, and the first frame 3110 may move forward and backward in the first direction for a distance corresponding to the length of the guide hole 3132.

Meanwhile, as shown in FIG. 15, the first frame 3110 may include a first part 3110a and a second part 3110b. For example, the second part 3110b may include the protrusion 3112, the first part 3110a may be inserted into the second part 3110b and pulled out from the second part 3110b, and the positions of the first part 3110a and the second part 3110b may be fixed by a fixing pin penetrating through side surfaces of the first part 3110a and the second part 3110b. Therefore, it is possible to finely adjust the position of the first seating portion 3113a for each user.

As shown in FIGS. 15 and 16, the second frame 3120 has a shape bent along the front surface and the bottom surface of the guide 3130 facing the second frame 3120, and the bottom surface may include a concave portion at which the second frame 3120 may be disposed. Also, the bottom surface of the guide 3130 includes a pair of convex protrusions 3134 located on both sides of the concave portion around the concave portion, and the second frame 3120 includes a fixing portion 3122 located between the pair of convex protrusions 3134 and aligned to the pair of convex protrusions 3134.

Meanwhile, the fixing portion 3122 and the pair of convex protrusions 3134 may be penetrated by one pin P arranged in a direction perpendicular to the first direction and be fixed in position. Therefore, the second frame 3120 may be rotated in the vertical direction around the pin P. Also, the spring S is located between the bottom surface of the guide 3130 and the second frame 3120, and thus the first frame 3110 and the second frame 3120 may be separated apart from each other in the vertical direction. The spring S may be located in a depression region 124 of the second frame 3120.

Therefore, even when the jaw loses strength during sleep and the mouth opens, the first seating portion 3113a and the second seating portion 3113b maintain close contacts with the upper teeth and the lower teeth of the user, respectively, thereby preventing separation of the driving unit 3100 and improving the effect of using the mandibular advancement device 30.

The intraoral device 3101 as described above is coupled to the power transmission unit 3102 and may be covered by a front cover 3150. The front cover 3150 prevents the guide 3130 from being exposed to the outside and may include a hole 3152 at the front, such that only the first frame 3110 and the second frame 3120 located in the oral cavity protrude to the outside. Here, a distance between the first frame 3110 and the second frame 3120 may be adjusted by the hole 3152. The front cover 3150 may include, for example, silicon.

The power transmission unit 3102 may include a body 3140 coupled to the intraoral device 3101, a cylinder 3160 coupled to the rear of the body 3140, a rear cover 3162 coupled to the cylinder 3160, the piston 3170 disposed inside the cylinder 3160, and a first dial 3142 and a second dial 3144 arranged to surround the outer surface of the body 3140.

The body 3140 has an empty space therein, and may have, for example, a cylindrical shape. A fastening protrusion 3146 for coupling with the guide 3130 protrudes from the front surface of the body 3140, and an opening 3141 through which a piston rod 3174 may penetrate when the piston 3170 moves is formed. As described above, since the piston rod 3174 is inserted into the opening 3141, the piston rod 3174 may be prevented from being tilted when the piston 3170 moves.

The rear cover 3162 to which the connection unit 300 is connected is coupled to the cylinder 3160, driving force generated by the main body 200 may be supplied to the cylinder 3160, and the piston 3170 may be moved toward the intraoral device 3101 by the driving force. For example, the driving force may be compressed air.

The piston 3170 may include a piston head 3172 disposed inside the cylinder 3160, the piston rod 3174 protruding from the center of the piston head 3172 toward the intraoral device 3101, and a plurality of support beams 3176 protruding from the piston rod 3174 in a direction perpendicular to a direction in which the piston rod 3174 extends. Here, the plurality means at least two. Although FIG. 14 shows an example in which a pair of support beams 3176 protrude from the piston rod 3174 in opposite directions and extend, the present disclosure is not limited thereto, and three or more support beams 3176 may be formed.

A sealing member for preventing air leakage may be located on the outer circumferential surface of the piston head 3172. The sealing member may be an O-ring. In another example, the piston head 3172 may be covered with a rubber material.

Meanwhile, a plurality of grooves G are formed in the body 3140. The plurality of grooves G may be spaced apart from one another at a certain distance in the circumferential direction of the body 3140 and may extend from one end of the body 3140 in the lengthwise direction of the body 3140. The plurality of support beams 3176 may be positioned in the grooves G.

When a driving force is applied to the piston 3170, the piston rod 3174 passes through the opening 3141 and pushes the first frame 3110 by the movement of the piston 3170.

On the other hand, as described above, the first seating portion 3113*a* on which the upper teeth of the user are seated is formed on the first frame 3110 coupled to the guide 3130 to be movable in the first direction, and the second frame 3120 partially buried by the second seating portion 3113*b* on which the lower teeth of the user are seated is coupled to the guide 3130 to not to be movable in the first direction, and the guide 3130 is coupled to the power transmission unit 3102. Also, the maxillary, in which the upper teeth are arranged, is fixed to the skull, whereas the mandible, in which the lower teeth are arranged, may be moved forward by the temporomandibular joint.

Therefore, when the piston rod 3174 pushes the first frame 3110, the position of the first frame 3110 is not changed substantially. Meanwhile, the second frame 3120, the guide 3130, and the body 3140 move backward in a direction opposite to a direction in which the piston 3170 moves as a reaction of the pushing, and thus the mandible of the user is advanced.

Referring back to FIG. 14, a first dial 3142 and a second dial 3144 may be further arranged on the body 3140. Meanwhile, although it is described in the present disclosure that the power transmission unit 3102 includes the first dial 3142 and the second dial 3144, the present disclosure is not limited thereto, and the power transmission unit 3102 may include either one of the first dial 3142 and the second dial 3144 or may include three or more dials. Also, since the first dial 3142 and the second dial 3144 may have substantially the same shape, only the first dial 3142 will be described below.

As shown in FIG. 17, the first dial 3142 may have a cylindrical shape to surround the outer circumferential surface of the body 3140, and the inner side surface may include a first region 3143*a* and a second region 3143*b* having different heights from each other. A boundary 3143 between the first region 3143*a* and the second region 3143*b* may be formed, such that a distance from any one edge thereof gradually decreases along the circumference of the first dial 3142. For example, although FIG. 17 shows an example in which the boundary 3143 between the first region 3143*a* and the second region 3143*b* is formed in a step-like shape having a smooth curve, the present disclosure is not limited thereto, and the boundary 3143 may be formed in a straight line shape.

The thickness of the first region 3143*a* is smaller than the thickness of the second region 3143*b*, and the support beams 3176 coupled to the grooves G of the body 3140 may contact the first region 3143*a*. Therefore, when the first dial 3142 is rotated, the support beams 3176 are gradually pushed by the second region 3143*b* at the boundary 3143 between the first region 3143*a* and the second region 3143*b* and move in straight lines along the grooves G. As a result, the first frame 3110 may be advanced. In other words, before supplying a driving force to the power transmission unit 3102, relative positions of the first frame 3110 and the second frame 3120 may be set according to a user.

Moreover, since the position of the first frame 3110 may be adjusted by using the first dial 3142 and the second dial 3144, the intraoral device 3101 may be used even when the main body 200 malfunctions or only the driving unit 3100 is carried, and, as will be described later, even when the operation of the driving unit 3100 stops for a certain period in consideration of the fatigue of a user, advancement of the mandible may be maintained to secure the minimum airway, thereby maintaining the function of preventing apnea.

Referring back to FIG. 14, the body 3140 includes the fastening protrusion 3146 protruding from the front surface to be coupled with the guide 3130, and a seating portion 136 into which the fastening protrusion 3146 may be inserted is formed at the guide 3130. The seating portion 136 may be an empty space located between the top surface and the bottom surface of the guide 3130.

On the other hand, an end portion 3138 of the guide 3130 facing toward the power transmission unit 3102 may have a round shape, and a priming surface 3148 from which a region including the fastening protrusion 3146 protrudes is formed on the front surface of the body 3140, wherein the priming surface 3148 may have a concavely round shape in correspondence to the end portion 3138 of the guide 3130.

Also, the fastening protrusion 3146 may include an end portion circular when viewed from above, and the guide unit 3130 may include a pair of latches 3182 surrounding the end portion of the fastening protrusion 3146 from both sides. Here, the pair of latches 3182 may receive a force by a pair of latch springs 3184 buried in the guide 3130, respectively, move and closed along side surfaces of the fastening protrusion 3146, and fastened to the fastening protrusion 3146.

Meanwhile, the pair of latches 3182 may have rounded outer surfaces in correspondence to the shape of the priming surface 3148 and may include locking protrusions 3183 protruding outward from ends of the outer surfaces. Therefore, when the latch springs 3184 are compressed by pressing the locking protrusions 3183 of the pair of latches 3182, the latches 3182 are opened from each other, and thus the fastening with the fastening protrusion 3146 may be released. In other words, since the intraoral device 3101 may be easily separated from the power transmission unit 3102, the first seating portion 3113*a* and the second seating portion 3113*b* located in the oral cavity may be easily cleaned.

Also, when the head of the user sleeping while wearing the intraoral device 3101 is significantly rotated as the sleeping position of the user is changed to the prone position, a force may be applied to a side of the driving unit 3100 and the teeth of the user holding the intraoral device 3101 may be damaged. However, according to the present disclosure, since the priming surface 3148 protruding outward has a concavely round shape, when a force is applied to a side of the driving unit 3100, any one of the locking protrusions 3183 is pressed by the priming surface 3148, and thus any one of the latch springs 3184 is compressed. At this time, when the latch spring 3184 is compressed by a certain force or more, the pair of latches 3182 are sufficiently opened, and thus the power transmission unit 3102 may be separated from the intraoral device 3101 to prevent the teeth of the user from being damaged.

The driving unit 3100 may further include the sensing unit 3127. For example, as shown in FIG. 15, the sensing unit 3127 may be located in the rear cover 126. However, the present disclosure is not limited thereto, and the position of the sensing unit 3127 may vary. For example, the sensing unit 1127 may be located in the front cover 3150.

The sensing unit 3127 may include a sensor capable of detecting biometric information of a user and a communication module capable of transmitting and receiving data to and from the main body 200. Also, the sensing unit 3127 may receive an oxygen saturation measured by at least one of the first seating portion 3113*a* and the second seating portion 3113*b*.

Also, the driving unit 3100 may include a sensor 3151 capable of determining a breathing state of a user. The sensor 3151 may include at least one of a temperature sensor and a pressure sensor. The temperature sensor may detect a change in the temperature of inhalation and exhalation during respiration of a user, and the pressure sensor may monitor a change in pressure during exhalation, and the changes may be transmitted to the sensing unit 3127. Therefore, a breathing state of the user may be determined. When the mandibular advancement device 30 is worn, the sensor 3151 as described above may be located at a location adjacent to the nose of the user, e.g., inside the upper end of the front cover 3150 as shown in FIG. 15.

The body 200 may include the first case 210, the main circuit board 220 mounted on the first case 210, and the second case 260 coupled to the first case 210. In addition, a display unit 270 is located on the second case 260, and the display unit 270 may be covered by a protection member 280.

The connection unit 300 transfers the air supplied from the main body 200 to the driving unit 3100. The connection unit 300 may include a material having a flexible property for the convenience of using the mandibular advancement device 30.

As described above, the mandibular advancement device 10 according to the present disclosure automatically operates only when obstructive sleep apnea is sensed during sleep or sleep apnea is highly likely to occur, and thus user discomfort caused by wearing the mandibular advancement device 10, e.g., pain and salivation, may be reduced. Also, since the main body 200 that generates a driving force is separated from the driving unit 100, the weight of the driving unit 100 is reduced, and thus discomfort caused by wearing the driving unit 100 may be reduced.

While the inventive concept has been described with reference to exemplary embodiments, it is to be understood that the inventive concept is not limited to the disclosed example embodiments, but, on the contrary, is intended to cover various modifications and equivalent arrangements included within the spirit and scope of the appended claims. Accordingly, the true scope of protection of the present disclosure should be determined by the technical idea of the appended claims.

The invention claimed is:

1. A mandibular advancement device comprising:
a driving unit comprising an intraoral device;
a main body configured to generate a driving force for driving the driving unit; and
a connection unit configured to connect the driving unit and the main body to transmit the driving force generated by the main body to the driving unit,
wherein the driving unit comprises a driving case having an empty space therein, a coupling unit having fixed thereto the intraoral device and coupled to a front of the driving case, and a rear cover coupled to a rear of the driving case and accommodating a piston therein,
the intraoral device comprises a first frame and a second frame located to overlap each other, a first seating portion covering a portion of the first frame located in an oral cavity of a user, a second seating portion covering a portion of the second frame located in the oral cavity of the user, and a fixing unit coupled to the first frame and the second frame,
the first frame is coupled to the fixing unit to be relative movable with respect to the second frame, the second frame is fixed to the fixing unit, and the fixing unit is fixed to the coupling unit,
wherein the piston comprises a piston head disposed in the rear cover and a push arm protruding from the center of the piston head toward the fixing unit, and,
when the piston is moved by the driving force, the push arm pushes the first frame, wherein the piston further comprises a fitting protrusion protruding in a direction perpendicular to a direction in which the push arm extends,
the driving unit further comprises a lower cover coupled to the bottom surface of the driving case and
a rod and a guide covering the rod are arranged on the lower cover, and
the guide comprises a hole extending in one direction, and the rod protrudes to the outside of the guide through the hole and is coupled with the fitting protrusion.

2. The mandibular advancement device of claim 1, wherein upper teeth of the user are seated on the first seating portion, and lower teeth of the user are seated on the second seating portion, and the second frame and the driving case are moved backward by a force pushing the first frame.

3. The mandibular advancement device of claim 1, wherein the driving unit further comprises a sensing unit configured to sense user information, and the main body comprises a control unit configured to control an operation of the driving unit according to a sensing result sensed by the sensing unit.

4. The mandibular advancement device of claim 3, wherein the driving force is compressed air, the main body further comprises a pump configured to generate the compressed air, a first pipe and a second pipe configured to transmit the compressed air from the pump to the connection unit, and a valve configured to block a flow of the compressed air between the first pipe and the second pipe, and the control unit controls the operation of the driving unit by controlling operations of the pump and the valve.

\* \* \* \* \*